(12) United States Patent
Hibner et al.

(10) Patent No.: US 11,744,607 B2
(45) Date of Patent: Sep. 5, 2023

(54) ULTRASONIC SURGICAL INSTRUMENT WITH BLADE REPLACEMENT FEATURES

(71) Applicant: Cilag GmbH International, Zug (CH)

(72) Inventors: John A. Hibner, Mason, OH (US); Richard C. Smith, Milford, OH (US); Catherine A. Corbett, Cincinnati, OH (US); Craig N. Faller, Batavia, OH (US); David A. Witt, Maineville, OH (US)

(73) Assignee: Cilag GmbH International, Zug (CH)

( * ) Notice: Subject to any disclaimer, the term of this patent is extended or adjusted under 35 U.S.C. 154(b) by 236 days.

(21) Appl. No.: 17/128,523

(22) Filed: Dec. 21, 2020

(65) Prior Publication Data

US 2021/0137553 A1    May 13, 2021

Related U.S. Application Data

(60) Continuation of application No. 16/174,320, filed on Oct. 30, 2018, now Pat. No. 10,973,542, which is a
(Continued)

(51) Int. Cl.
*A61B 17/32* (2006.01)
*A61N 7/02* (2006.01)
(Continued)

(52) U.S. Cl.
CPC ........ *A61B 17/320092* (2013.01); *A61N 7/02* (2013.01); *A61B 2017/0042* (2013.01);
(Continued)

(58) Field of Classification Search
CPC .. A61B 2017/0042; A61B 2017/00477; A61B 2018/00619; A61B 2018/0063;
(Continued)

(56) References Cited

U.S. PATENT DOCUMENTS

| 5,322,055 A | * | 6/1994 | Davison ........ A61B 17/320068 |
| | | | 606/171 |
| 5,873,873 A | | 2/1999 | Smith et al. |

(Continued)

FOREIGN PATENT DOCUMENTS

| CN | 104023657 A | 9/2014 |
| EP | 2380511 A2 | 10/2011 |

(Continued)

OTHER PUBLICATIONS

Brazilian Search Report dated Jun. 18, 2020, for Application No. BR112018012563-6, 4 pages.
(Continued)

*Primary Examiner* — Julian W Woo
(74) *Attorney, Agent, or Firm* — Frost Brown Todd LLP

(57) ABSTRACT

An apparatus includes a shaft assembly and an end effector. The shaft assembly includes a first coupling member and a second coupling member. The first coupling member and the second coupling member are configured to flex toward each other from a first position to a second position. The first coupling member and the second coupling member define a pivot axis in the first position. The end effector includes an ultrasonic blade and a clamp arm. The clamp arm is configured to couple or decouple with the shaft assembly when the first coupling member and the second coupling member are in the second position. The clamp arm is configured to pivot toward and away the ultrasonic blade about the pivot axis when the first coupling member and the second coupling member are in the first position.

20 Claims, 34 Drawing Sheets

Related U.S. Application Data division of application No. 14/976,127, filed on Dec. 21, 2015, now Pat. No. 10,231,749.

(51) Int. Cl.
| | |
|---|---|
| A61B 17/00 | (2006.01) |
| A61B 17/29 | (2006.01) |
| A61B 90/00 | (2016.01) |
| A61B 18/00 | (2006.01) |
| A61N 7/00 | (2006.01) |

(52) U.S. Cl.
CPC .............. *A61B 2017/00389* (2013.01); *A61B 2017/00455* (2013.01); *A61B 2017/00477* (2013.01); *A61B 2017/00526* (2013.01); *A61B 2017/2926* (2013.01); *A61B 2017/2931* (2013.01); *A61B 2017/2947* (2013.01); *A61B 2017/320093* (2017.08); *A61B 2017/320094* (2017.08); *A61B 2018/0063* (2013.01); *A61B 2018/00589* (2013.01); *A61B 2018/00619* (2013.01); *A61B 2090/0808* (2016.02); *A61B 2090/0811* (2016.02); *A61B 2090/0813* (2016.02); *A61N 2007/0056* (2013.01)

(58) Field of Classification Search
CPC .... A61B 2090/0808; A61B 2090/0811; A61N 2007/0056
See application file for complete search history.

(56) References Cited

U.S. PATENT DOCUMENTS

| | | | |
|---|---|---|---|
| 5,935,144 | A | 8/1999 | Estabrook |
| 5,944,737 | A | 8/1999 | Tsonton et al. |
| 5,980,510 | A | 11/1999 | Tsonton et al. |
| 6,254,623 | B1 | 7/2001 | Haibel, Jr. et al. |
| 6,283,981 | B1 | 9/2001 | Beaupre |
| 6,309,400 | B2 | 10/2001 | Beaupre |
| 6,325,811 | B1 | 12/2001 | Messerly |
| 6,423,082 | B1 | 7/2002 | Houser et al. |
| 6,432,118 | B1 | 8/2002 | Messerly |
| 6,558,376 | B2 | 5/2003 | Bishop |
| 6,773,444 | B2 | 8/2004 | Messerly |
| 6,783,524 | B2 | 8/2004 | Anderson et al. |
| 7,544,200 | B2 | 6/2009 | Houser |
| 8,057,498 | B2 | 11/2011 | Robertson |
| 8,231,644 | B2 | 7/2012 | Onaga |
| 8,328,834 | B2 | 12/2012 | Isaacs et al. |
| 8,461,744 | B2 | 6/2013 | Wiener et al. |
| 8,591,536 | B2 | 11/2013 | Robertson |
| 8,623,027 | B2 | 1/2014 | Price et al. |
| 8,911,460 | B2 | 12/2014 | Neurohr et al. |
| 9,023,071 | B2 | 5/2015 | Miller et al. |
| 9,039,720 | B2 * | 5/2015 | Madan .................. G16H 20/40 606/169 |
| 9,095,367 | B2 | 8/2015 | Olson et al. |
| 9,314,261 | B2 | 4/2016 | Bales, Jr. et al. |
| 9,345,506 | B2 * | 5/2016 | Stoddard ........ A61B 17/320092 |
| 9,351,754 | B2 | 5/2016 | Vakharia et al. |
| 9,474,887 | B2 | 10/2016 | Navis |
| 9,743,946 | B2 | 8/2017 | Faller et al. |
| 9,782,214 | B2 | 10/2017 | Houser et al. |
| 10,231,749 | B2 | 3/2019 | Hibner et al. |
| 10,881,448 | B2 * | 1/2021 | Houser ............. A61B 17/2812 |
| 10,973,542 | B2 | 4/2021 | Hibner et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0147092 | A1 | 6/2008 | Rogge et al. |
| 2008/0200940 | A1 | 8/2008 | Eichmann et al. |
| 2012/0112687 | A1 | 5/2012 | Houser et al. |
| 2012/0116265 | A1 | 5/2012 | Houser et al. |
| 2014/0005701 | A1 | 1/2014 | Olson et al. |
| 2014/0330298 | A1 | 11/2014 | Arshonsky et al. |
| 2016/0015419 | A1 | 1/2016 | Hibner et al. |

FOREIGN PATENT DOCUMENTS

| | | |
|---|---|---|
| EP | 2641552 A2 | 9/2013 |
| JP | 2007-048566 A | 2/2007 |
| JP | 2013-545536 A | 12/2013 |

OTHER PUBLICATIONS

Chinese Office Action, Notification of the First Office Action, and First Search, dated Jun. 24, 2020, for Application No. 201680074970. 3, 8 pages.

International Search Report and Written Opinion dated Sep. 22, 2017, for Application No. PCT/US2016/066451, 20 pages.

Japanese Office Action, Notice of Reasons for Refusal, and First Search Report by Registered Search Organization, dated Dec. 8, 2020, for Application No. 2018-550656, 26 pages.

U.S. Appl. No. 61/410,603, entitled "Energy-Based Surgical Instruments," filed Nov. 5, 2010.

\* cited by examiner

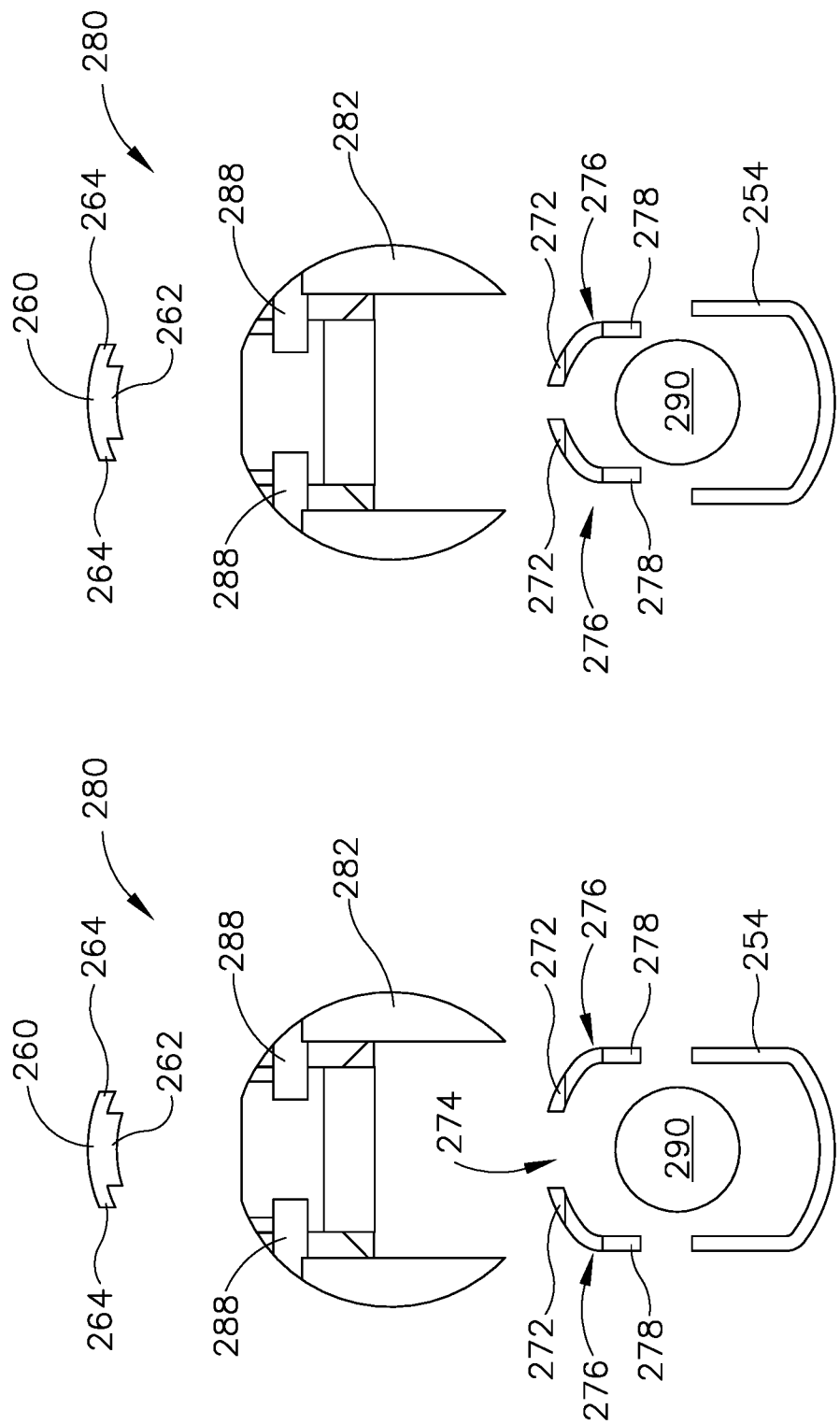

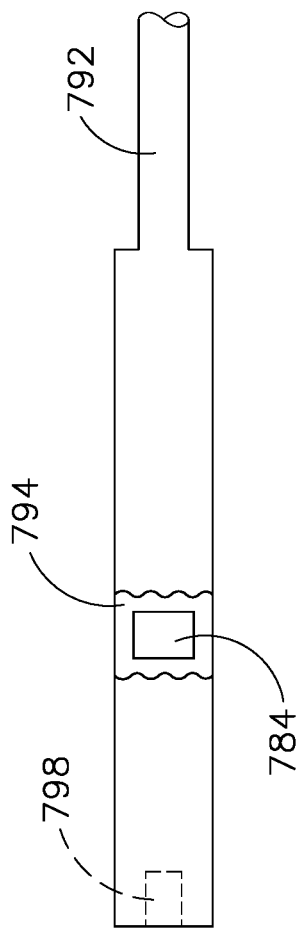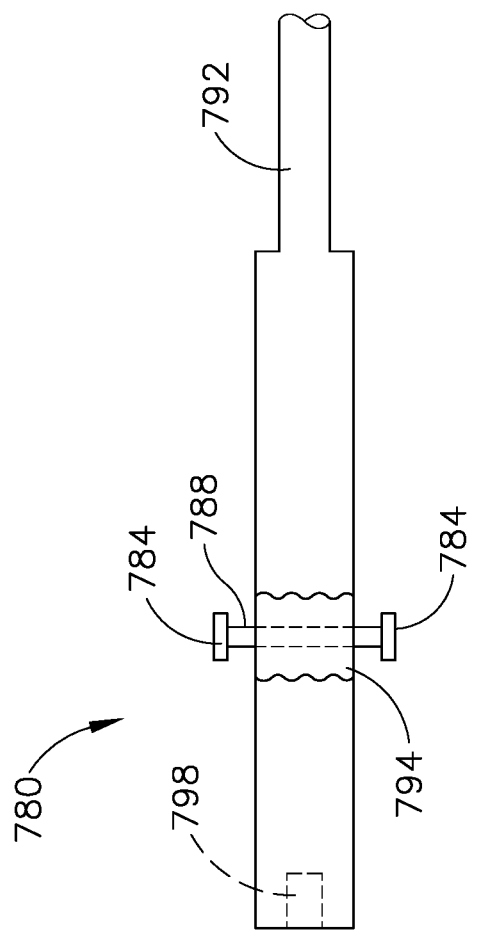

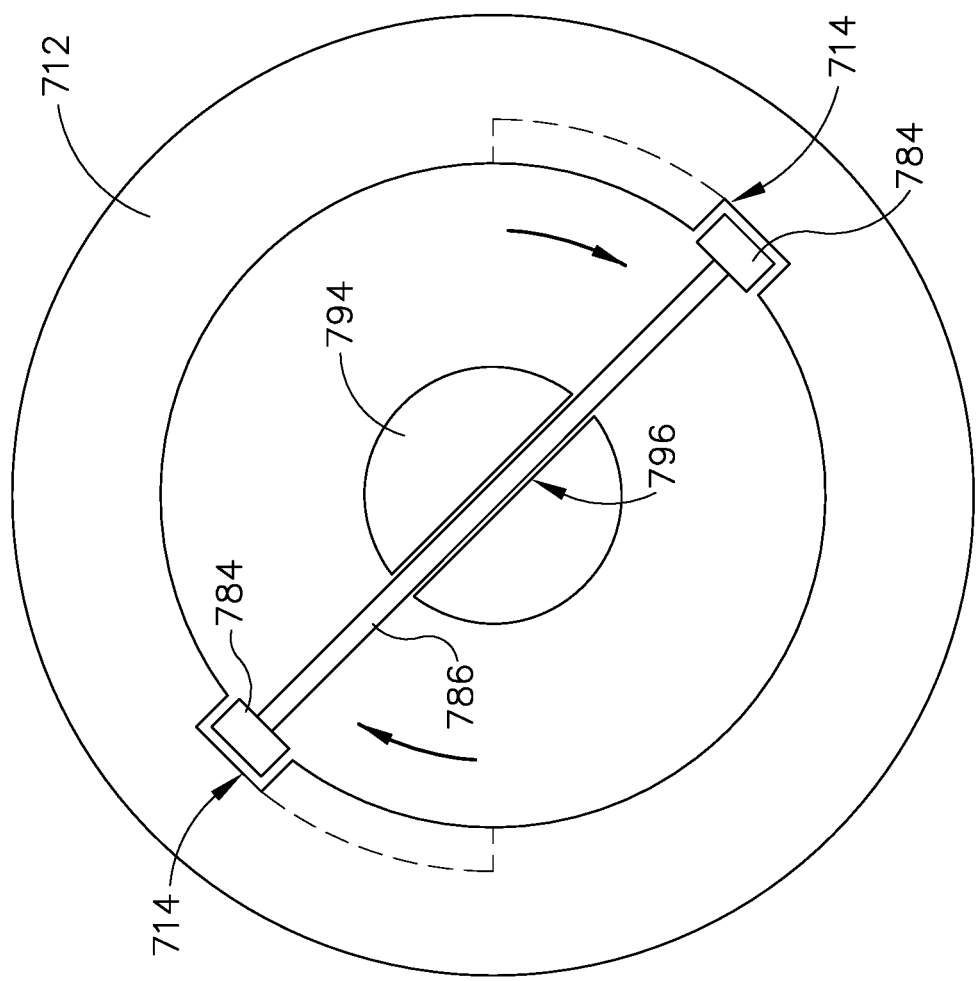

ULTRASONIC SURGICAL INSTRUMENT WITH BLADE REPLACEMENT FEATURES

This application is a continuation of U.S. patent application Ser. No. 16/174,320, entitled "Ultrasonic Surgical Instrument with Blade Replacement Features," filed Oct. 30, 2018 and published as U.S. Pub. No. 2019/0125395 on May 2, 2019, issued as U.S. Pat. No. 10,973,542 on Apr. 13, 2021, which is a divisional of U.S. patent application Ser. No. 14/976,127, filed Dec. 21, 2015 and issued as U.S. Pat. No. 10,231,749 on Mar. 19, 2019, entitled "Ultrasonic Surgical Instrument with Blade Replacement Features."

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, now U.S. Pat. No. 8,911,460, issued Dec. 16, 2014, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," now U.S. Pat. No. 9,393,037, issued Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 10A depicts front cross-sectional view of the end effector of FIG. 8A, where the clamp arm is detached from the inner and outer tube of the shaft assembly;

FIG. 10B depicts a front cross-sectional view of the end effector of FIG. 8A, where the clamp arm is detached from the inner and outer tube of the shaft assembly, where the distal prongs of the inner tube are pressed toward each other;

FIG. 23 depicts a top plan view of the waveguide and clocking pin of FIG. 19;

FIG. 24 depicts a side elevational view of the waveguide and clocking pin of FIG. 19;

FIG. 26B depicts a cross-sectional view, taken along line 26B-26B of FIG. 25B, of the waveguide and clocking pin of FIG. 19 being initially inserted into the threaded shroud of disposable assembly of FIG. 19;

Figure 1:
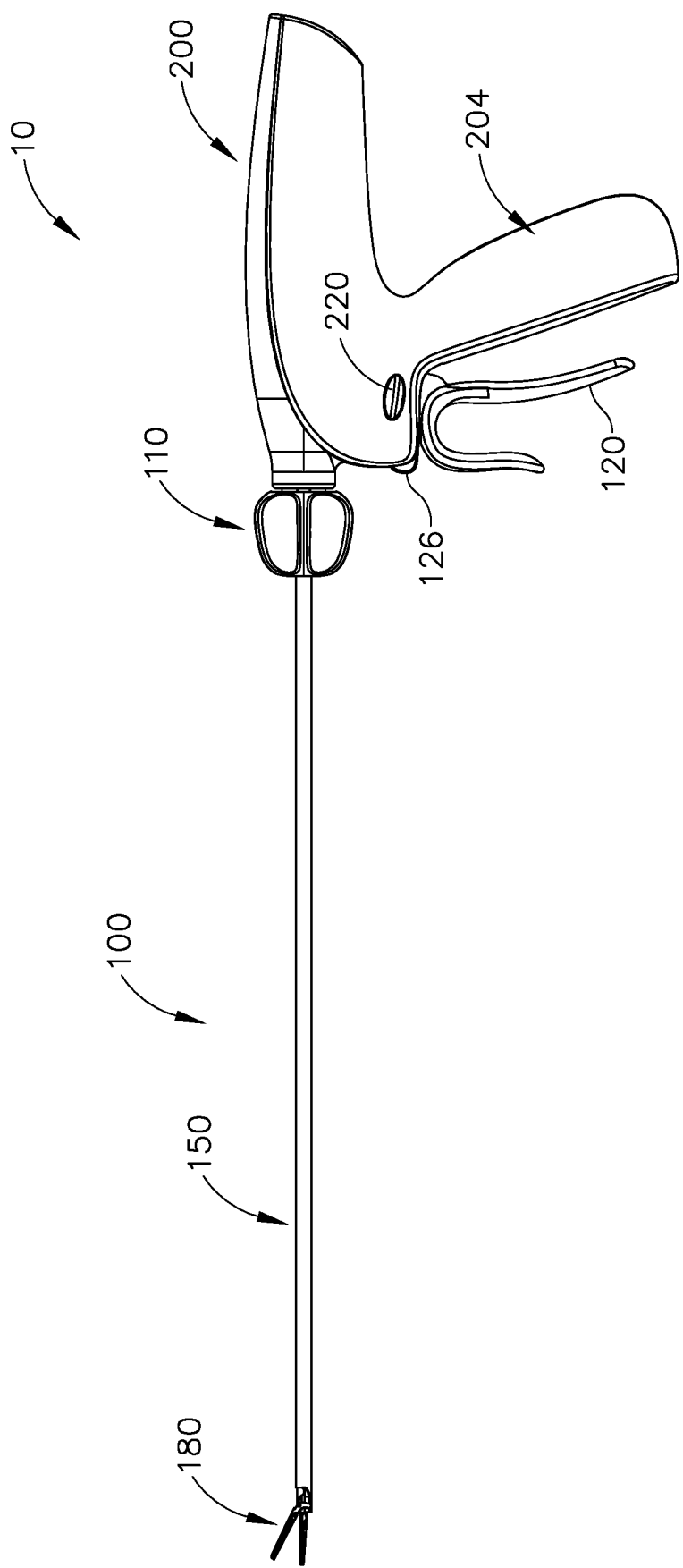
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instrument

Figure 2:
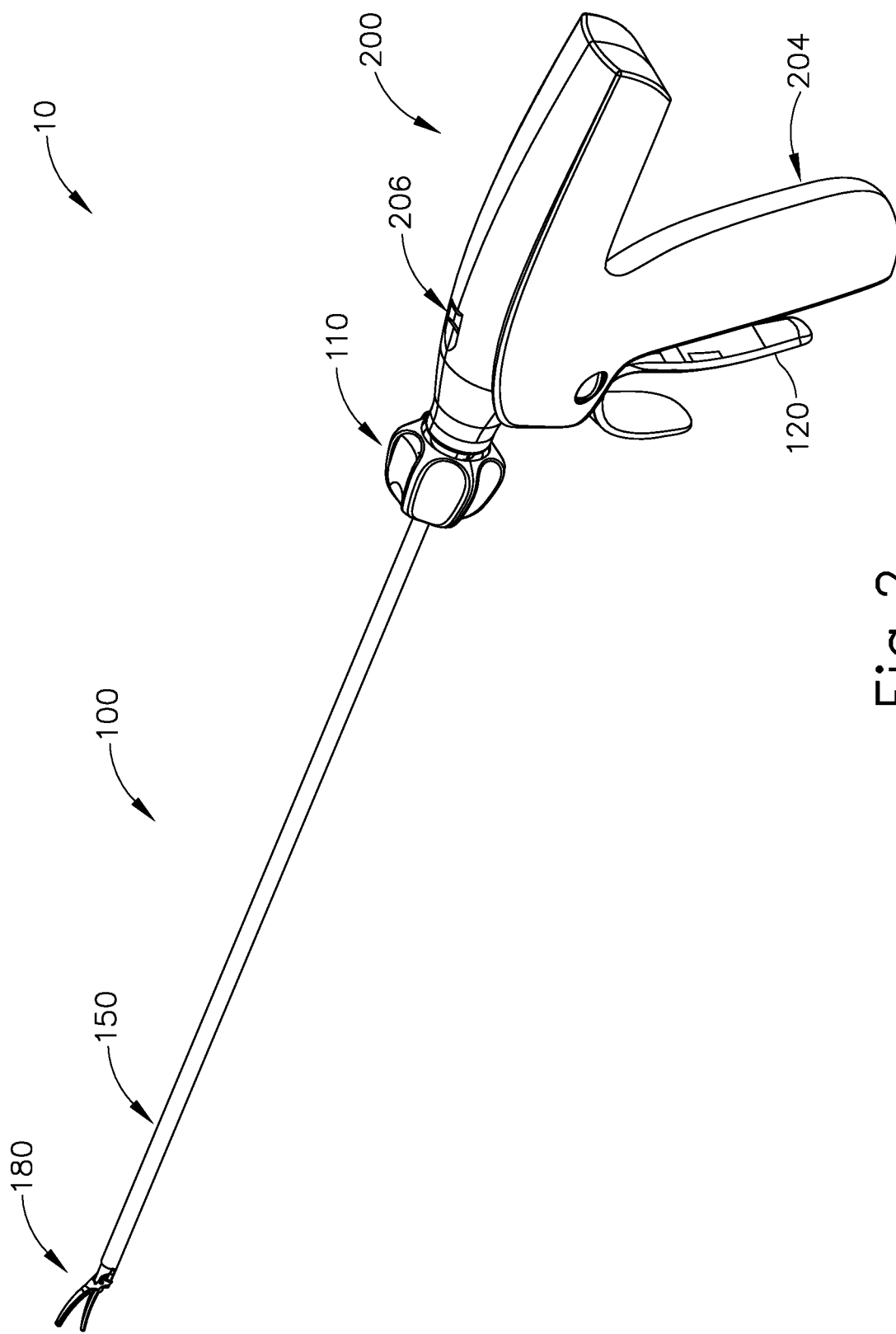
FIG. 2 depicts a perspective view of the instrument of FIG. 1.
Figure 3:
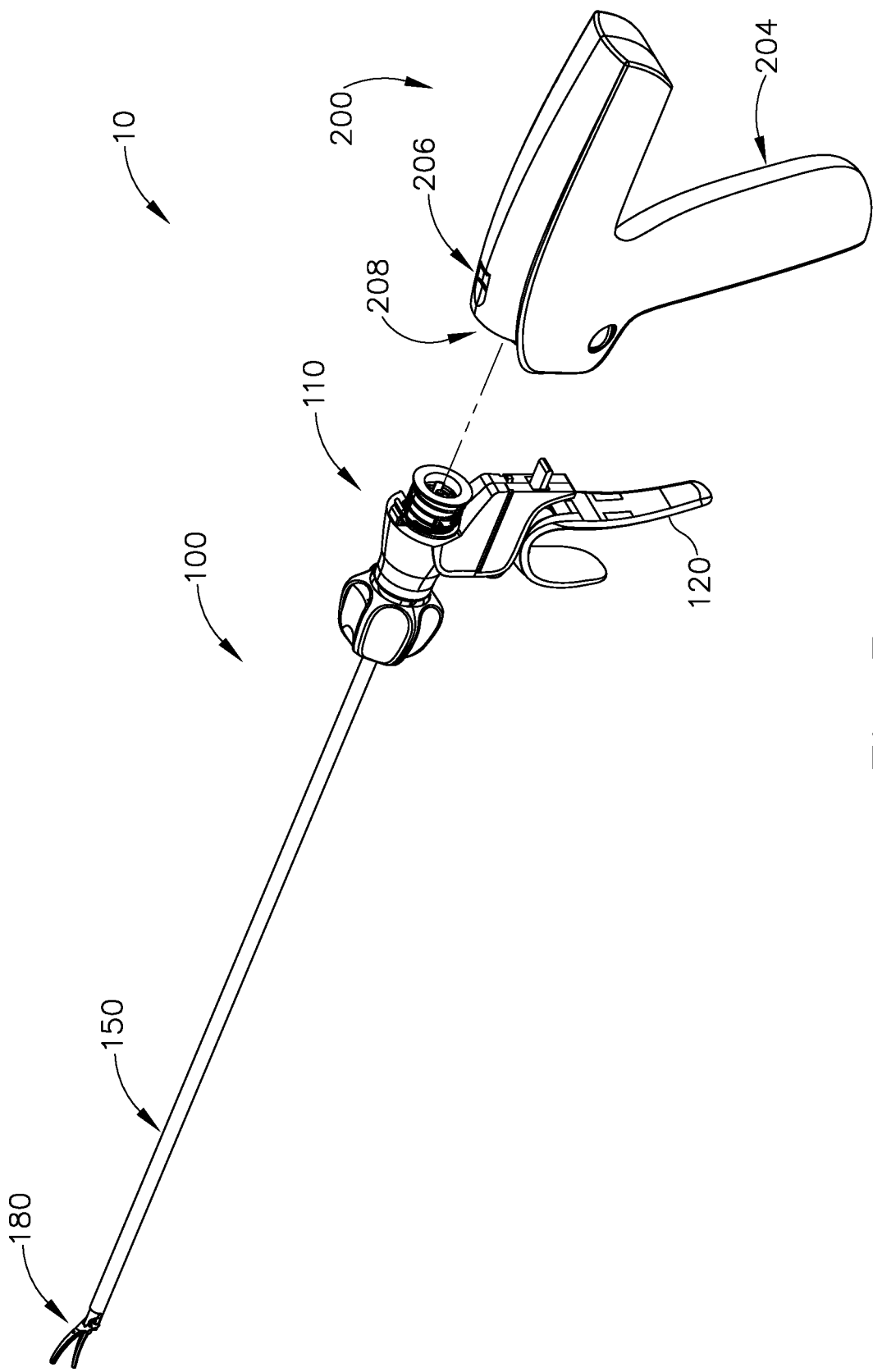
FIG. 3 depicts a perspective view of the instrument of FIG. 1, with a disposable portion separated from a reusable portion.
Figure 4:
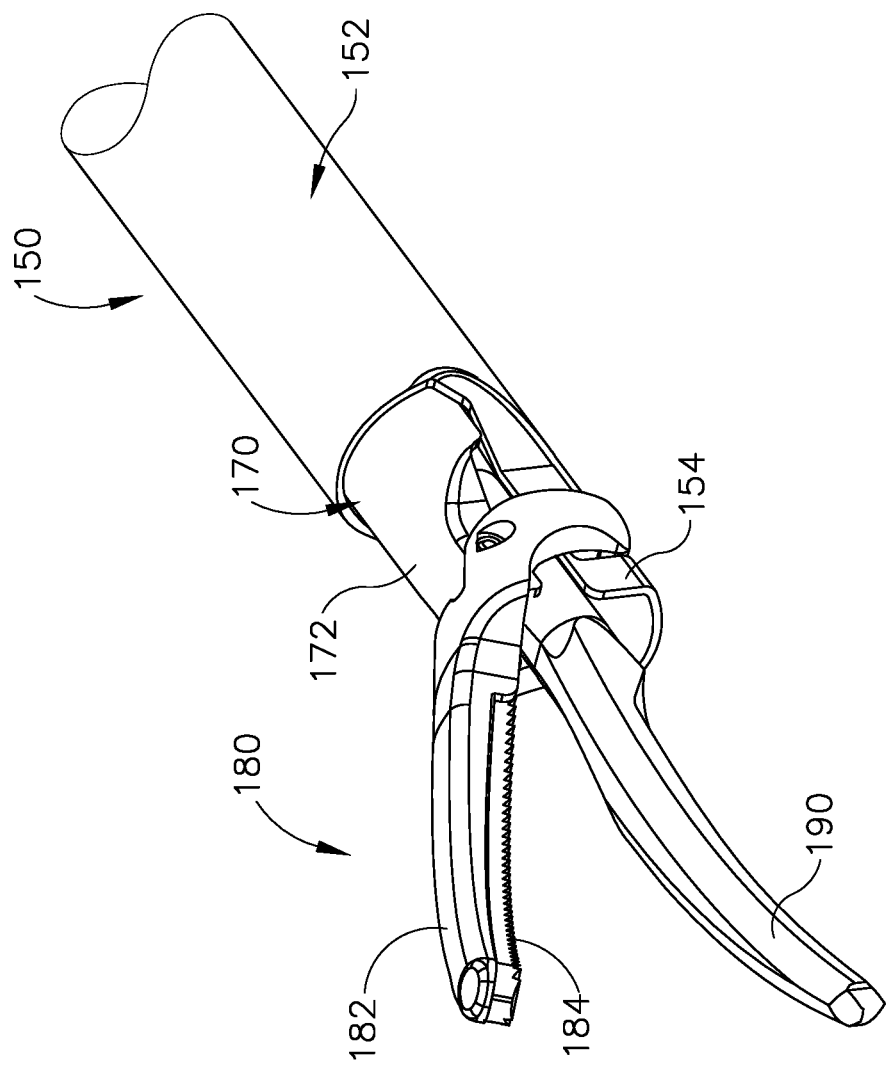
FIG. 4 depicts a perspective view of an end effector of the instrument of FIG. 1, in an open configuration.

FIGS. 1-3 show an exemplary ultrasonic surgical instrument (10) that is configured to be used in minimally invasive surgical procedures (e.g., via a trocar or other small diameter access port, etc.). As will be described in greater detail below, instrument (10) is operable to cut tissue and seal or weld tissue (e.g., a blood vessel, etc.) substantially simultaneously. Instrument (10) of this example comprises a disposable assembly (100) and a reusable assembly (200). The distal portion of reusable assembly (200) is configured to removably receive the proximal portion of disposable assembly (100), as seen in FIGS. 2-3, to form instrument (10).

In an exemplary use, assemblies (100, 200) are coupled together to form instrument (10) before a surgical procedure, the assembled instrument (10) is used to perform the surgical procedure, and then assemblies (100, 200) are decoupled from each other for further processing. In some instances, after the surgical procedure is complete, disposable assembly (100) is immediately disposed of while reusable assembly (200) is sterilized and otherwise processed for re-use. By way of example only, reusable assembly (200) may be sterilized in a conventional relatively low temperature, relatively low pressure, hydrogen peroxide sterilization process. Alternatively, reusable assembly (200) may be sterilized using any other suitable systems and techniques (e.g., autoclave, etc.). In some versions, reusable assembly (200) may be sterilized and reused approximately 100 times. Alternatively, reusable assembly (200) may be subject to any other suitable life cycle. For instance, reusable assembly (200) may be disposed of after a single use, if desired. While disposable assembly (100) is referred to herein as being "disposable," it should be understood that, in some instances, disposable assembly (100) may also be sterilized and otherwise processed for re-use. By way of example only, disposable assembly (100) may be sterilized and reused approximately 2-30 times, using any suitable systems and techniques. Alternatively, disposable assembly (100) may be subject to any other suitable life cycle.

Figure 6A:
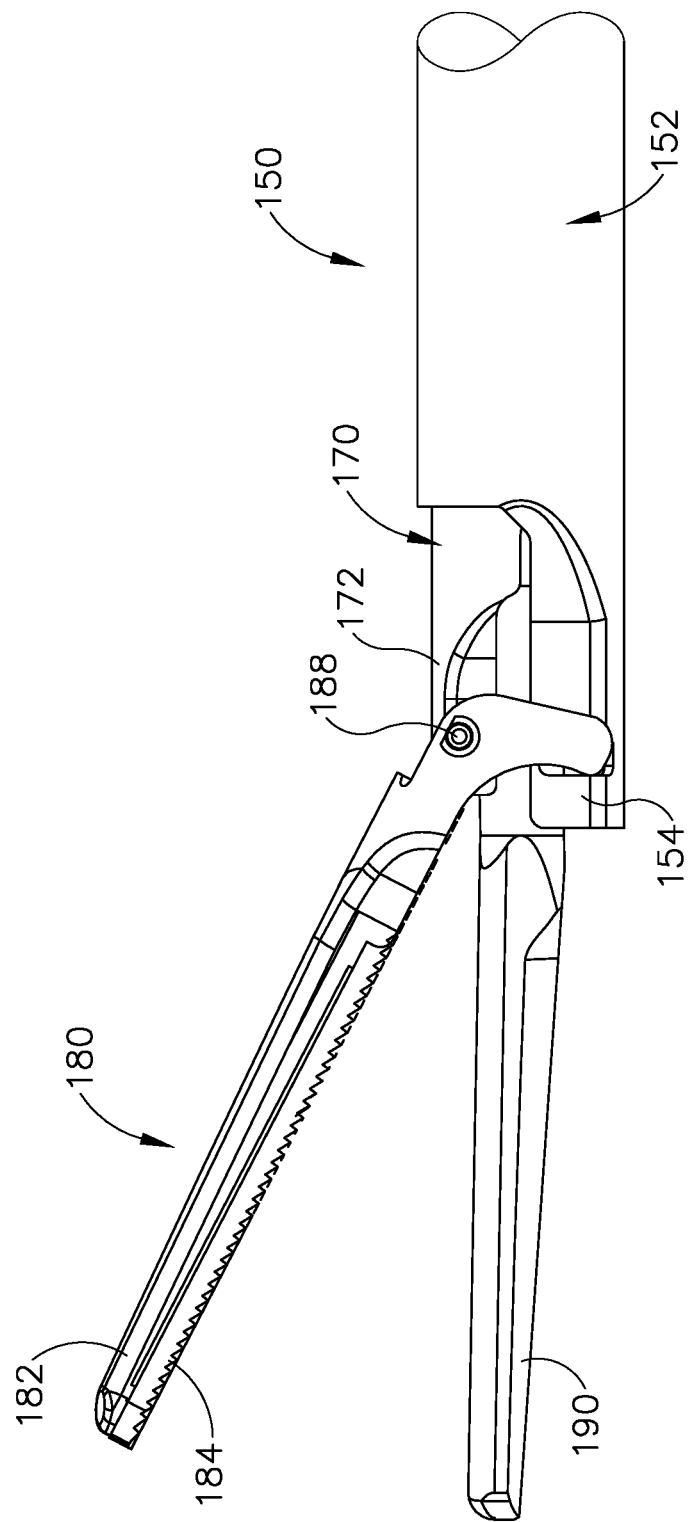
FIG. 6A depicts a side elevational view of the end effector of FIG. 4, in the open configuration.
Figure 6B:
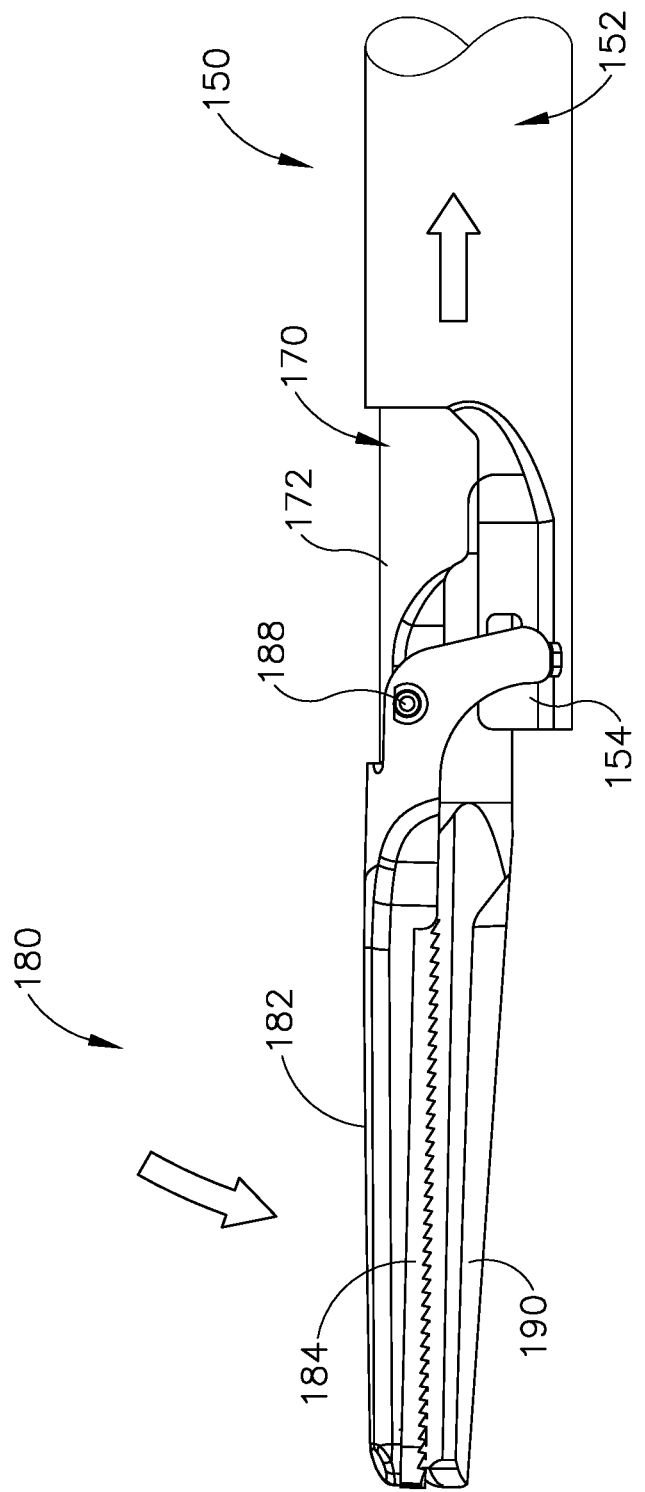
FIG. 6B depicts a side elevational view of the end effector of FIG. 4, in a closed configuration.
Figure 7:
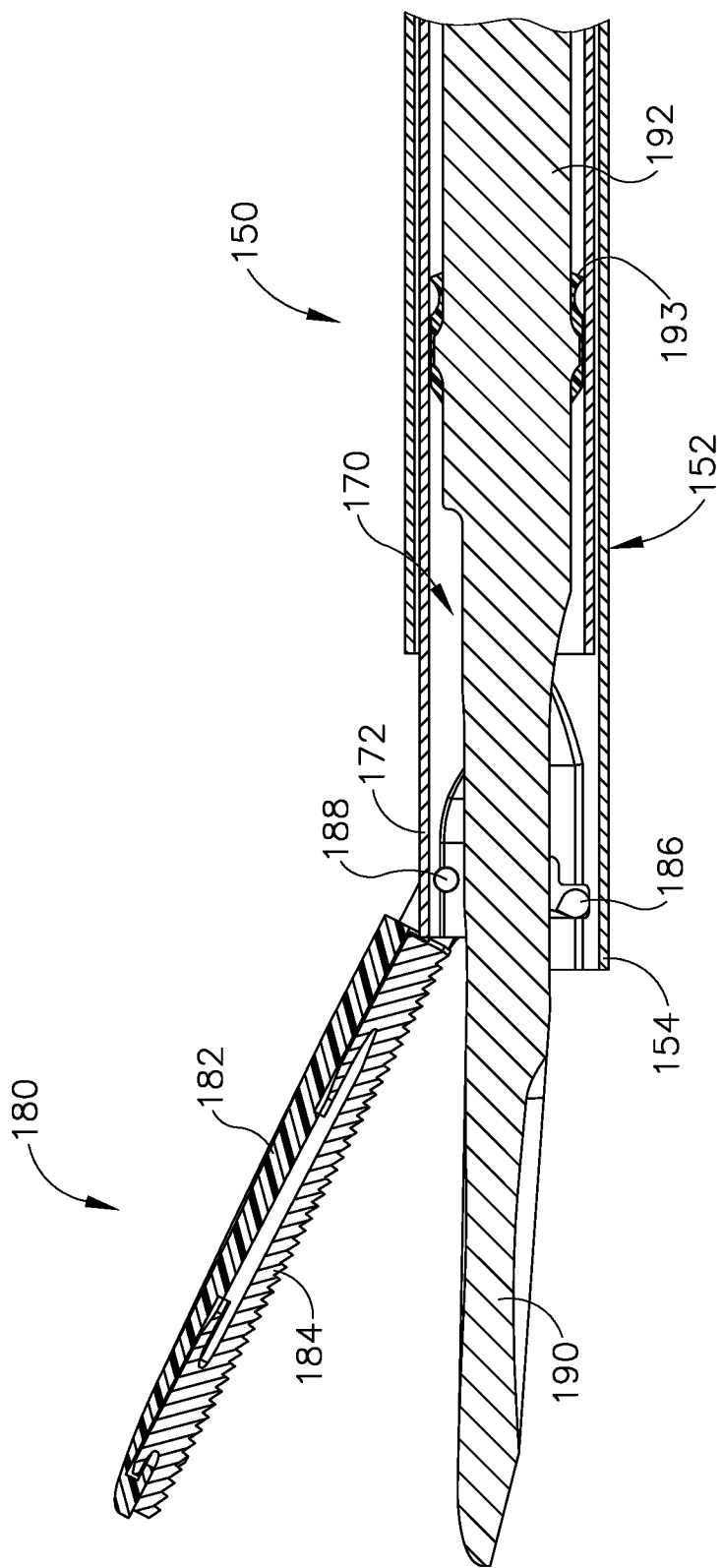
FIG. 7 depicts a side cross-sectional view of the end effector of FIG. 4, in the open configuration.

Disposable assembly (100) of the present example comprises a body portion (110), a shaft assembly (150) extending distally from body portion (110), and an end effector (180) located at the distal end of shaft assembly (150). As best seen in FIGS. 4-7, end effector (180) of this example comprises a clamp arm (182) and an ultrasonic blade (190). Clamp arm (182) includes a clamp pad (184), which faces blade (190). As shown in FIGS. 6A-6B, clamp arm (182) is pivotable toward and away from blade (190) to selectively compress tissue between clamp pad (184) and blade (190). As seen in FIG. 7, blade (190) is an integral feature of the distal end of an acoustic waveguide (192), which extends coaxially through tubes (152, 170), and which is configured to communicate ultrasonic vibrations to blade (190).

Shaft assembly (150) comprises an outer tube (152) and an inner tube (170). Outer tube (152) is operable to translate longitudinally relative to inner tube (170) to selectively pivot clamp arm (182) toward and away from blade (190).

Figure 5:
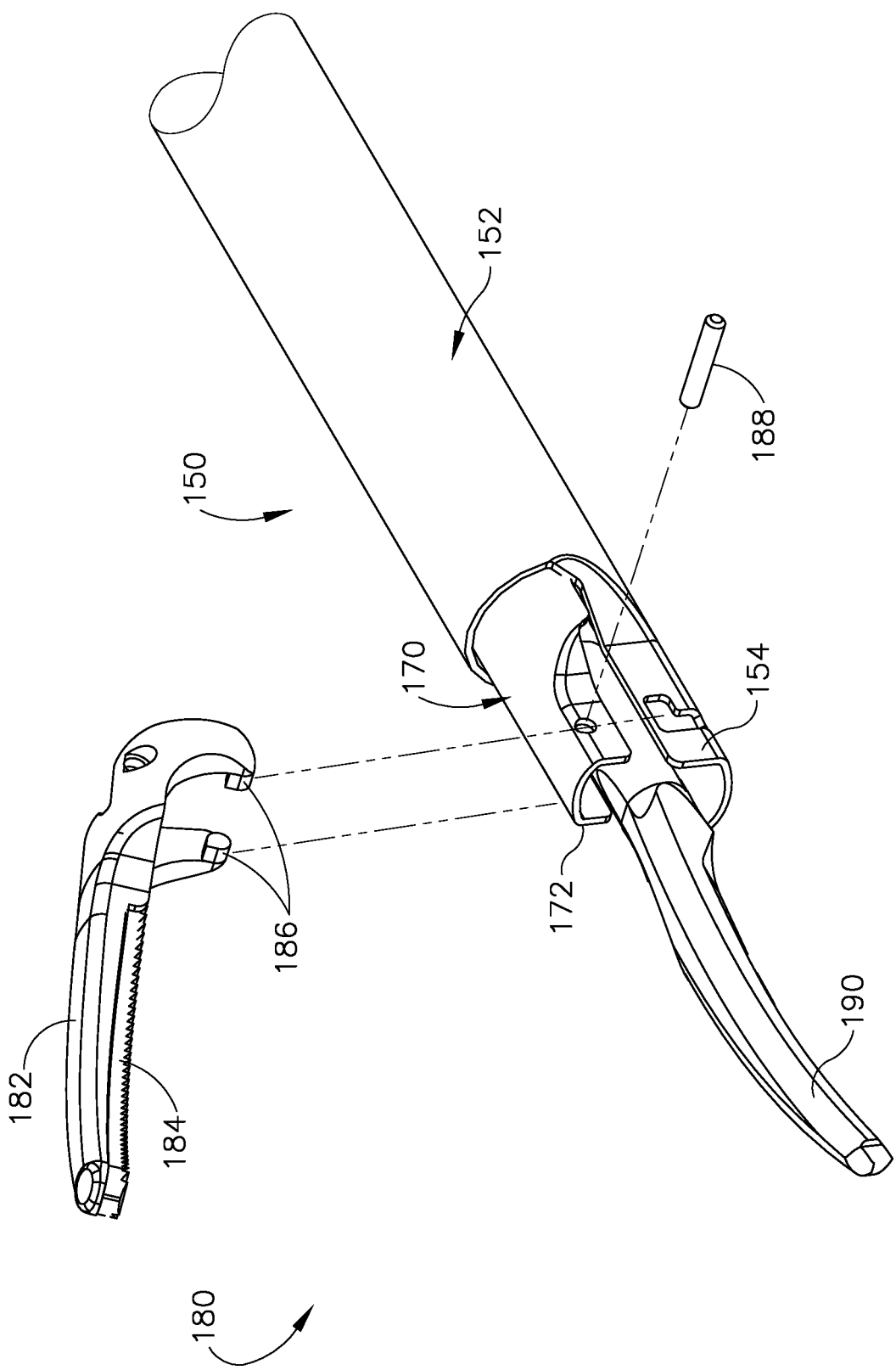
FIG. 5 depicts a partially exploded view of the end effector of FIG. 4.

To accomplish this, and as best seen in FIGS. 5 and 7, integral pin features (186) of clamp arm (182) pivotally secure a first portion of clamp arm (182) to a distally projecting tongue (154) of outer tube (152); while an inserted pin (188) pivotally secures a second portion of clamp arm (182) to a distally projecting tongue (172) of inner tube (170). Thus, as can be seen in the transition from FIG. 6A to FIG. 6B, tubes (152, 170) cooperate to pivot clamp arm (182) toward blade (190) when outer tube (152) is retracted proximally relative to inner tube (170). It should be understood that clamp arm (182) may be pivoted back away from blade (190) (e.g., from the position shown in FIG. 6B to the position shown in FIG. 6A) by translating outer tube (152) distally relative to inner tube (170), in reverse of the operation shown in FIGS. 6A-6B. In an exemplary use, clamp arm (182) may be pivoted toward blade (190) to grasp, compress, seal, and sever tissue captured between clamp pad (184) and blade (190). Clamp arm (182) may be pivoted away from blade (190) to release tissue from between clamp pad (184) and blade (190); and/or to perform blunt dissection of tissue engaging opposing outer surfaces of clamp arm (182) and blade (190). In some alternative versions, inner tube (170) is translated and outer tube (152) remains stationary to provide actuation of clamp arm (182).

Reusable assembly (200) includes a pistol grip (204) in this example, though it should be understood that any other suitable kind of grip may be used. A trigger (120) of reusable assembly (200) is configured to pivot toward and away from pistol grip (204) to thereby translate outer tube (152), to thereby pivot clamp arm (182). Buttons (126, 220) of reusable assembly (200) are operable to activate blade (190) to cause blade (190) to vibrate at ultrasonic frequencies. In some versions, at least one button (126, 220) is also operable to activate end effector (180) to deliver RF electrosurgical energy to tissue. Reusable assembly (200) also includes a battery (not shown), a generator (not shown), an ultrasonic transducer assembly (not shown), and a torque wrench assembly (not shown). The battery (not shown) is operable to provide electrical power to the generator (not shown); the generator (not shown) is operable to provide electrical power to the ultrasonic transducer assembly (not shown); the ultrasonic transducer assembly is operable to convert electrical power into ultrasonic vibrations; and the torque wrench assembly (not shown) is operable to mechanically and acoustically couple waveguide (192) with the ultrasonic transducer assembly (not shown). All of these components and operabilities may be provided in accordance with at least some of the teachings of U.S. patent application Ser. No. 14/868,574, entitled "Ultrasonic Surgical Instrument with Removable Handle Assembly," filed Sep. 29, 2015, published as U.S. Pub. No. 2016/0015419 on Jan. 21, 2016, issued as U.S. Pat. No. 10,349,967 on Jul. 16, 2019, the disclosure of which is incorporated by reference herein.

When waveguide (192) is sufficiently coupled with the transducer assembly (not shown), ultrasonic vibrations that are generated by the transducer assembly (not shown) are communicated along waveguide (192) to reach blade (190). In the present example, the distal end of blade (190) is located at a position corresponding to an anti-node associated with resonant ultrasonic vibrations communicated through waveguide (192), in order to tune the acoustic assembly to a preferred resonant frequency $f_o$ when the acoustic assembly is not loaded by tissue. When the transducer assembly (not shown) is energized, the distal end of blade (190) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer assembly (not shown) of the present example is activated, these mechanical oscillations are transmitted through waveguide (192) to reach blade (190), thereby providing oscillation of blade (190) at the resonant ultrasonic frequency. Thus, when tissue is secured between blade (190) and clamp pad (184), the ultrasonic oscillation of blade (190) may simultaneously sever the tissue and denature the proteins in adjacent tissue cells, thereby providing a coagulative effect with relatively little thermal spread. In some versions, an electrical current may also be provided through blade (190) and/or clamp pad (184) to also seal the tissue.

Other aspects of disposable assembly (100) and reusable assembly (200) may be provided in accordance with at least some of the teachings of U.S. patent application Ser. No. 14/868,574, published as U.S. Pub. No. 2016/0015419 on Jan. 21, 2016, issued as U.S. Pat. No. 10,349,967 on Jul. 16, 2019, and/or any of the other references that are cited herein. Further exemplary features and operabilities for disposable assembly (100) and reusable assembly (200) will be described in greater detail below, while other variations will be apparent to those of ordinary skill in the art in view of the teachings herein.

II. Exemplary Alternative Clamp Arm Attachment Features

Some operators may use blade (190) to perform back-cutting operations, where the underside of blade (190) is pressed against tissue to sever the tissue without using clamp arm (182) to compress the tissue. The resulting lateral forces on blade (190) may cause blade (190) and/or waveguide (192) to deflect slightly laterally. This may present a risk of blade (190) contacting pin (188), which may be undesirable. It may therefore be desirable to reconfigure end effector (180) such that pin (188) is not laterally adjacent to blade (190). In addition to reducing metal-to-metal contact risks associated with back-cutting, reconfiguring pin (188) may also facilitate longitudinal translation of blade (190) and waveguide (192) relative to the rest of shaft assembly (150) and end effector (180), such as when an operator wishes to clean or replace blade (190) and waveguide (192).

Those of ordinary skill in the art will also recognize that a clamp pad (184) may tend to wear after use, such that it may be desirable to replace clamp pad (184). To accomplish this, it may be beneficial to remove clamp arm (182) from tubes (152, 170). In the configuration of end effector (180), some operators may have difficulty removing pin (188) in order to enable removal of clamp arm (182) from tubes (152, 170). It may therefore be desirable to reconfigure end effector (180) to make it easier to remove clamp arm (182) from tubes (152, 170), such as by modifying the configuration of pin (188).

The examples below relate to various alternative configurations that may be incorporated into end effector (180). At least some of these alternative configurations may reduce metal-to-metal contact risks associated with back-cutting, facilitate longitudinal translation of blade (190) and waveguide (192) relative to the rest of shaft assembly (150) and end effector (180), and/or facilitate removal of clamp arm (182) from tubes (152, 170). In addition or in the alternative, the below described alternative configurations may provide other benefits. It should be understood that the following examples are merely illustrative.

A. Permanent Retention Clip

Figure 8A:
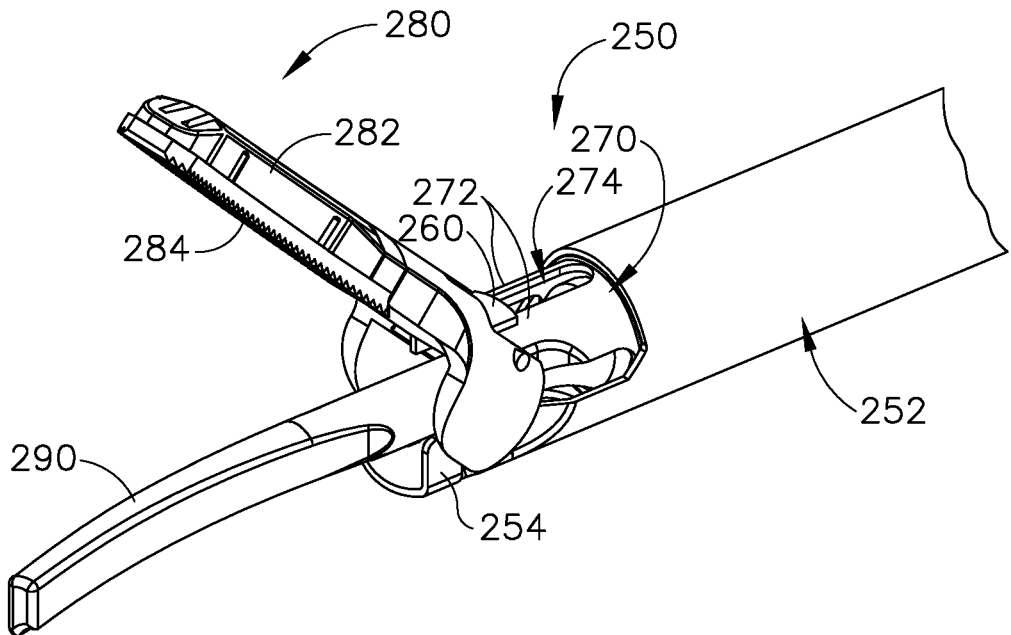
FIG. 8A depicts a perspective view of an alternative end effector and an alternative shaft assembly that may be readily incorporated into the instrument of FIG. 1, where the end effector is in the open position.
Figure 8B:
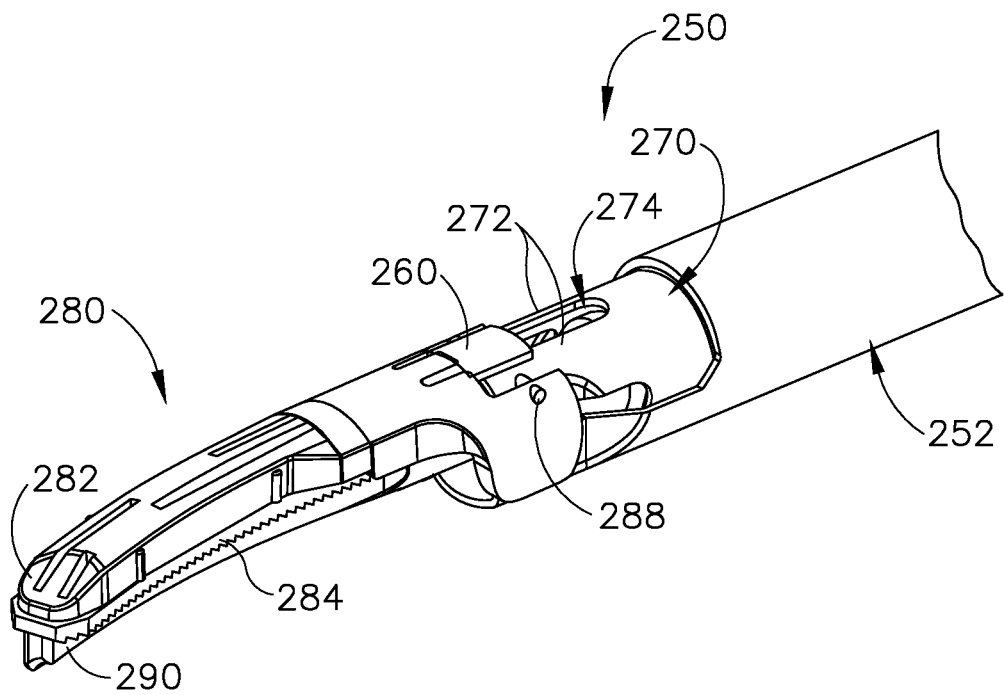
FIG. 8B depicts a perspective view of the end effector and shaft assembly of FIG. 8A, where the end effector is in the closed position.
Figure 9:
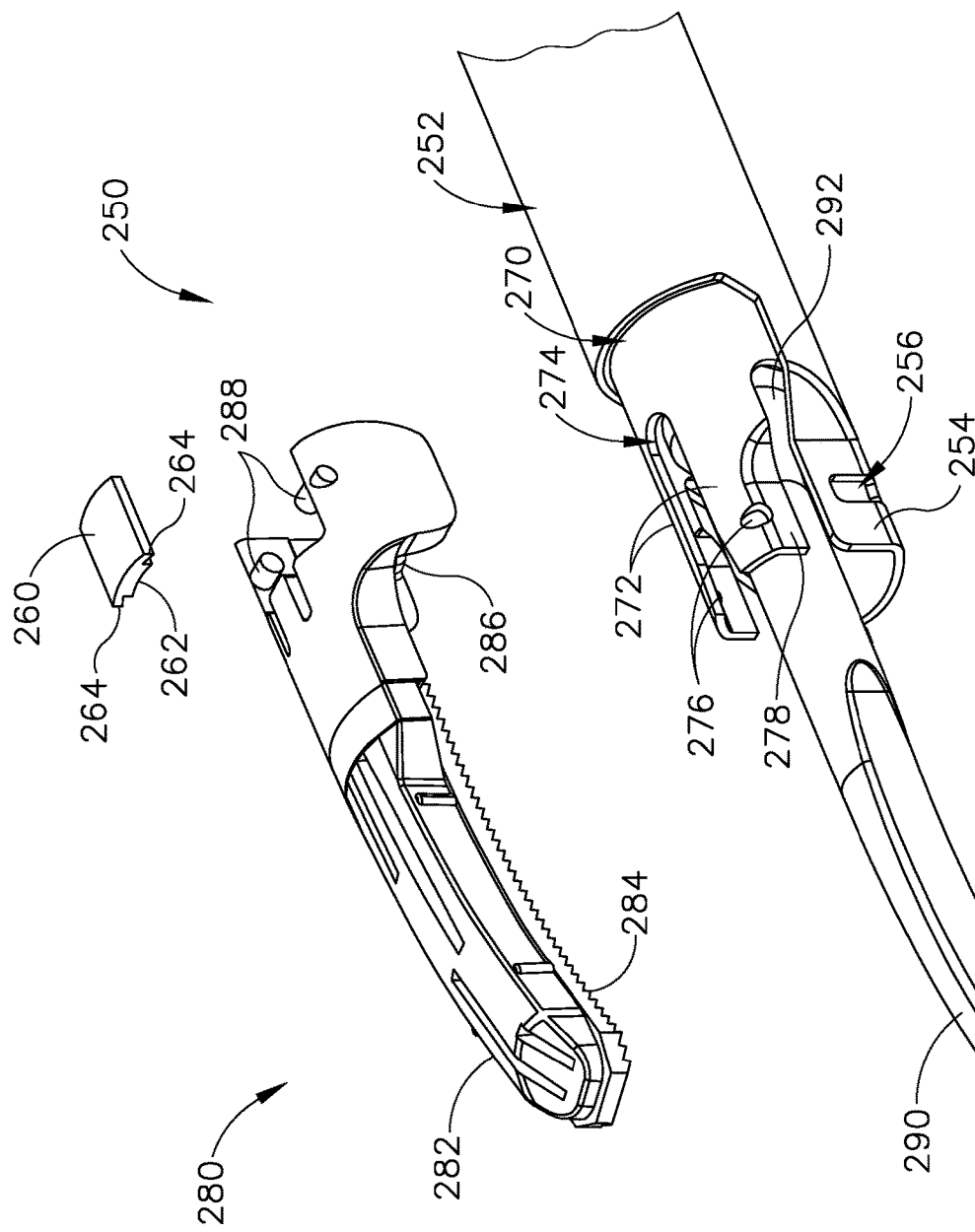
FIG. 9 depicts an exploded perspective view of the end effector and shaft assembly of FIG. 8A.

FIGS. 8A-9 show an alternative shaft assembly (250) and alternative end effector (280) that may be readily incorporated into instrument (10) described above in place of shaft assembly (150) end effector (180). End effector (280) includes a clamp arm (282) and a clamp pad (284) that are substantially similar to clamp arm (182) and clamp pad (184) described above, with differences described in detail below. As best seen in FIG. 9, shaft assembly (250) includes an outer tube (252), an inner tube (270), and an acoustic waveguide (292) extending through both outer tube (252) and inner tube (270). Outer tube (252), inner tube (270), and acoustic waveguide (292) are substantially similar to outer tube (152), inner tube (170), and acoustic waveguide (192) mentioned above, respectively, with differences described below.

As best seen in FIGS. 8A-8B, outer tube (252) is operable to translate longitudinally relative to inner tube (270) to selectively pivot clamp arm (282) toward and away from blade (290). To accomplish this, and as best seen in FIG. 9, integral pin features (286) of clamp arm (282), which are substantially similar to integral pin features (186) mentioned above, pivotally secure a first portion of clamp arm (282) to pin slot (256) of a distally projecting tongue (254) of outer tube (252); while integral pin features (288) pivotally secure a second portion of clamp arm (282) to angled distal prongs (272) of inner tube (270) via pin holes (276). It should be understood that integral pin features (286) may vertically translate within pin slot (256). Therefore, longitudinal translation of outer tube (252) rotates the first portion of clamp arm (282) about the second portion of clamp arm (282). Thus, as can be seen in the transition from FIG. 8A to FIG. 8B, tubes (252, 270) cooperate to pivot clamp arm (282) toward blade (290) when outer tube (252) is retracted proximally relative to inner tube (270). It should be understood that clamp arm (282) may be pivoted back away from blade (290) (e.g., from the position shown in FIG. 8B to the position shown in FIG. 8A) by translating outer tube (252) distally relative to inner tube (270), in reverse of the operation shown in FIGS. 8A-8B. In an exemplary use, clamp arm (282) may be pivoted toward blade (290) to grasp, compress, seal, and sever tissue captured between clamp pad (282) and blade (290). Clamp arm (282) may be pivoted away from blade (290) to release tissue from between clamp pad (282) and blade (290); and/or to perform blunt dissection of tissue engaging opposing outer surface of clamp arm (282) and blade (290).

While inner tube (170) includes distally projecting tongue (172), inner tube (270) of the present example includes a pair of angled distal prongs (272) defining a longitudinal channel (274). Angled distal prongs (272) each have a flat surface (278) extending from prongs (272). Together, each angled distal prong (272) and corresponding flat surface (278) define a pin hole (276). As will be described in greater detail below, pin holes (276) are dimensioned to receive integral pins (288) of clamp arm (282). As also seen in FIG. 9, end effector (280) further includes a cap (260). Cap (260) includes a spacer (262) and a pair of flanges (264). Spacer (262) is dimensioned with fit within longitudinal channel (274) while flanges (264) are dimensioned to rest on top of angled distal prongs (272). As will be described in further detail below, cap (260) is configured to fix integral pins (288) within pin holes (276) once clamp arm (282) is assembled to inner tube (270).

Figures 10C, 10D:
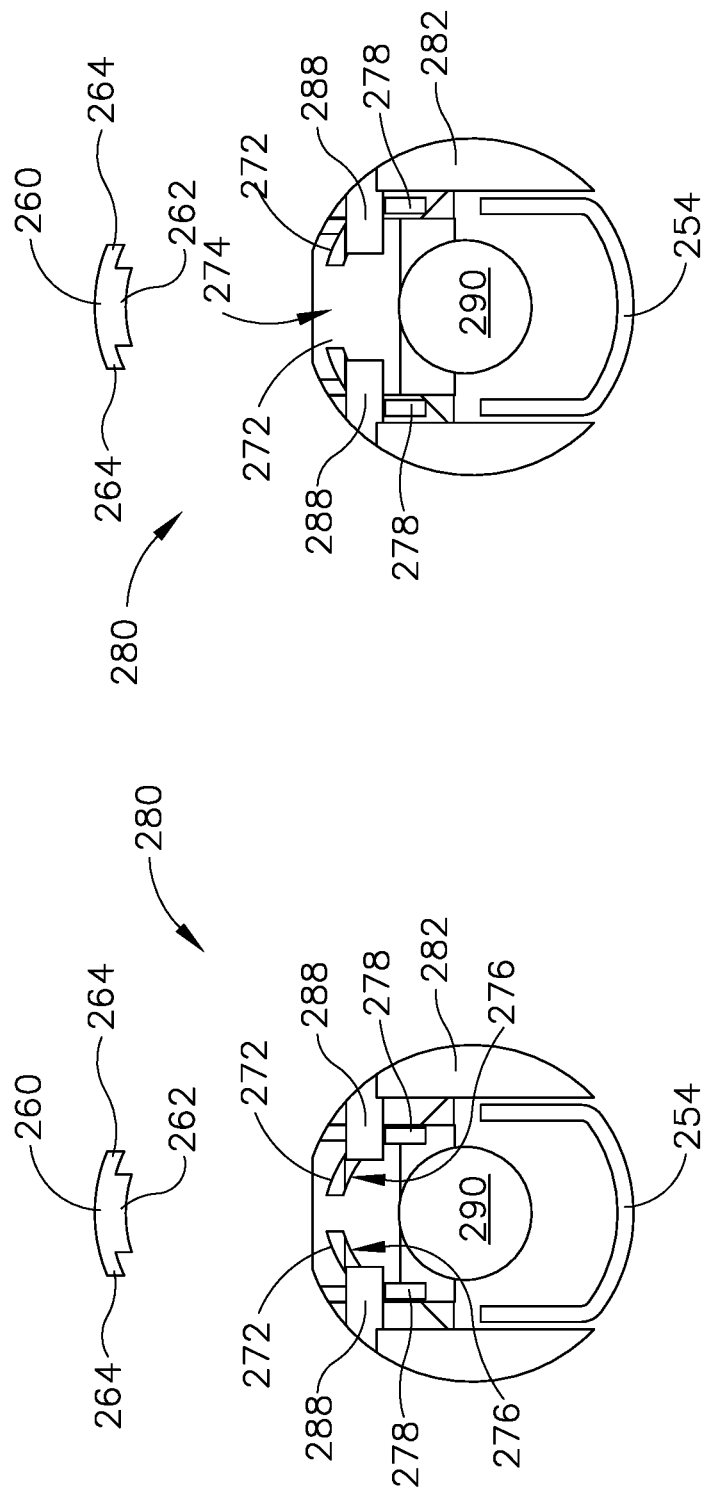
FIG. 10C depicts a front cross-sectional view of the end effector of FIG. 8A, where the clamp arm is attached to the inner and outer tube of the shaft assembly, where the distal prongs of the inner tube are pressed toward each other.
FIG. 10D depicts a front cross-sectional view of the end effector of FIG. 8A, where the clamp arm is attached to the inner and outer tube of the shaft assembly, where the distal prongs of the inner tube engage the integral pins of the clamp arm.

FIGS. 10A-10E show an exemplary assembly of clamp arm (282) and inner tube (270). As best seen in FIG. 10A, clamp arm (282) is placed over angled distal prongs (272) such that integral pins (288) are laterally aligned with angled distal prongs (272). It should be understood that inner tube (270) is made out of a resilient material, such that angled distal prongs (272) may flex relative to one another within longitudinal channel (274). Therefore, as seen in FIG. 10B, a user may pinch angled distal prongs (272) or flats (278) together, such that angled distal prongs (272) flex toward each other within longitudinal channel (274). Integral pins (288) and angled distal prongs (272) are then no longer laterally aligned, but both angled distal prongs (272) are laterally between integral pins (288).

With angled distal prongs (272) deflected inwardly, and as seen in FIG. 10C, the operator may place clamp arm (282) over inner tube (270) such that integral pins (288) slide past angled distal prongs (272) within pin holes (276). Integral pins (288) abut against flats (278). At this stage, integral pins (288) are within pin holes (276). As seen in FIG. 10D, the operator may now release angled distal prongs (272) and/or flats (278). Due to the resilient nature of angled distal prongs (272) and flats (278), both angled distal prongs (272) and flats (278) return to their natural position, as shown in FIG. 10D. Additionally, integral pins (288) abut against both angled distal prongs (272) and flats (278). Integral pins (288) are now fixed within pin holes (276) at this stage.

Figure 10E:
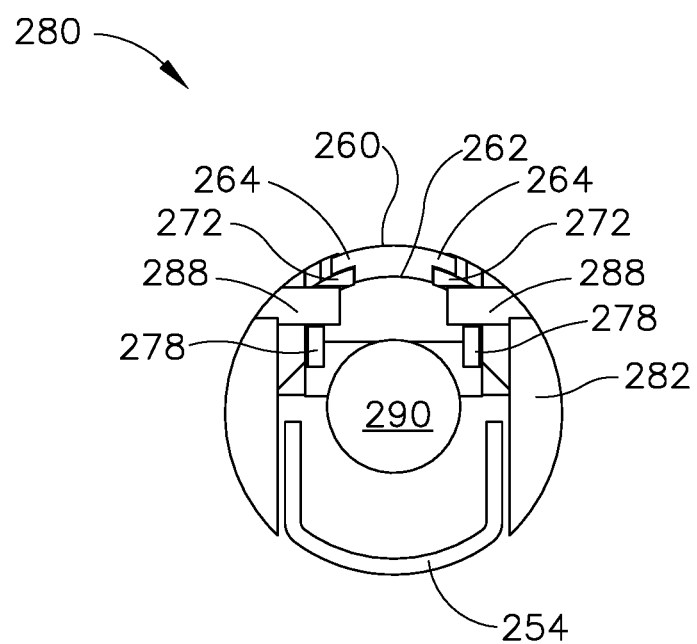
FIG. 10E depicts a front cross-sectional view of the end effector of FIG. 8A completely assembled.

With integral pins (288) located in pin holes (276), and as shown in FIG. 10E, cap (260) is then placed on top of inner tube (270) such that spacer (262) lies within longitudinal channel (274) while abutting against both angled distal prongs (272). Additionally, flanges (264) rest on top angled distal prongs (272). With cap (260) in place, angled distal prongs (272) and/or flats (278) are no longer capable of deflecting inwardly toward one another within longitudinal channel (274) to release integral pins (288) from pin holes (276). At this point, cap (260) may be welded to angled distal prongs (272) to fix cap (260) to inner tube (270), and therefore fix clamp arm (282) to inner tube (270). Of course, any other suitable method of fixing cap (260) to angled distal prongs (272) may be used as would be apparent to one having ordinary skill in the art in view of the teachings herein. It should be understood that integral pins (288) do not extend laterally across the width of inner tube (270). Additionally, integral pins (288) are dimensioned to not extend across the lateral width of blade (290). Therefore, the chances of blade (290) making contact with integral pins (288) are reduced or eliminated.

While an operator flexes angled distal prongs (272) and/or flats (278) toward one another as a separate step of the process in the present example, it should be understood that this is merely optional. In some alternative versions, the operator may force integral pins (288) on top of angled distal prongs (272), and contact between integral pins (288) and angled distal prongs (272) may provide a camming action that flexes distal prongs (272) and flats (278) toward each other. In some such versions, integral pins (288) may have angled surfaces that cooperate with angled distal prongs (272) to further promote this camming action. Other ways that angled distal prongs (273) and flats (278) may flex toward each other to create the appropriate gap for insertion of integral pins (288) into pin holes (276) will be apparent to one having ordinary skill in the art in view of the teachings herein.

B. Permanent Retention Tab

Figure 11A:
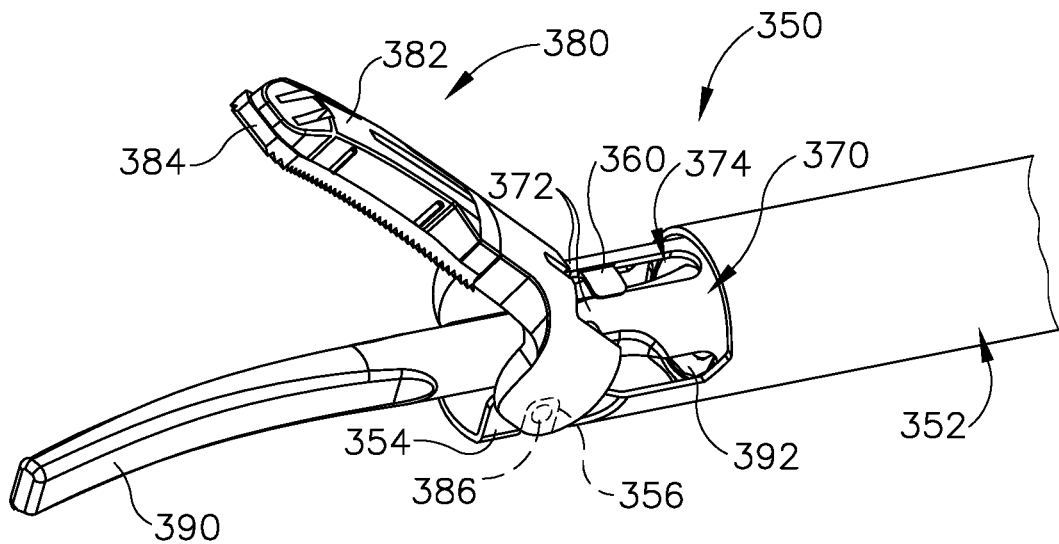
FIG. 11A depicts a perspective view of an another alternative end effector and an another alternative shaft assembly that may be readily incorporated into the instrument of FIG. 1, where the end effector is in the open position.
Figure 11B:
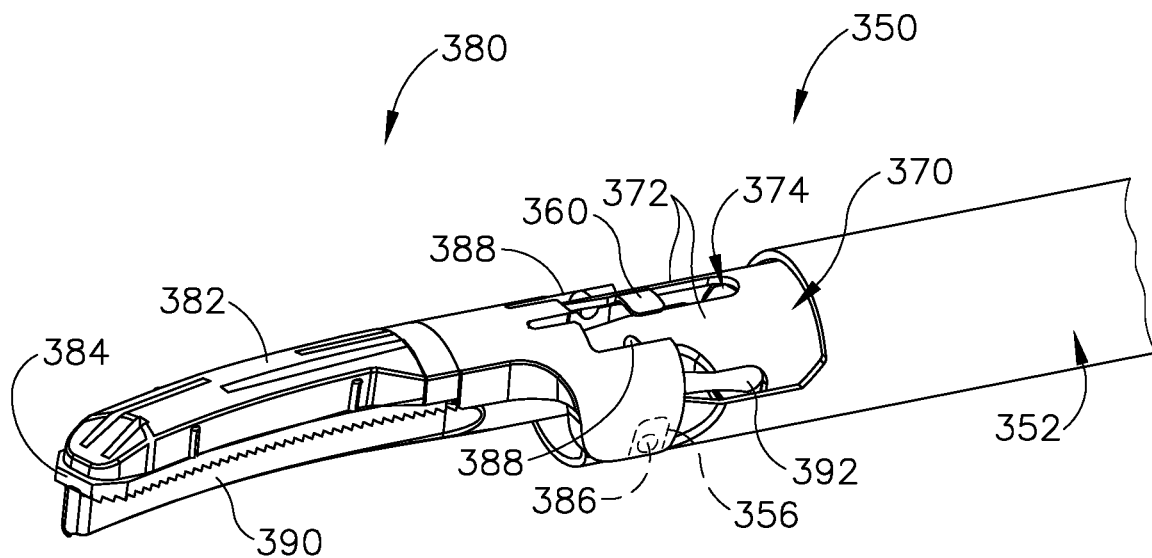
FIG. 11B depicts a perspective view of the end effector and shaft assembly of FIG. 11A, where the end effector is in the closed position.

FIGS. 11A-11B show another alternative shaft assembly (350) and alternative end effector (380) that may be readily incorporated into instrument (10) described above in place of shaft assembly (150) end effector (180). End effector (380) includes a clamp arm (382) and clamp pad (384) that are substantially similar to clamp arm (182) and clamp pad (184) described above, with difference described in detail below. Shaft assembly (350) includes an outer tube (352), an inner tube (370), and an acoustic waveguide (392) extending through both outer tube (352) and inner tube (370). Outer tube (252), inner tube (270), and acoustic waveguide (292) are substantially similar to outer tube (152), inner tube (170), and acoustic waveguide (192) mentioned above, respectively, with differences described below.

As best seen in FIGS. 11A-11B, outer tube (352) is operable to translate longitudinally relative to inner tube (370) to selectively pivot clamp arm (382) toward and away from blade (390). To accomplish this, integral pin features (386) of clamp arm (382), which are substantially similar to integral pin features (186) mentioned above, pivotally secure a first portion of clamp arm (382) to pin slot (356) of a distally projecting tongue (354) of outer tube (352); while integral pin features (388) pivotally secure a second portion of clamp arm (382) to angled distal prongs (372) of inner tube (370) via pin holes (376). It should be understood that integral pin features (386) may vertically translate within pin slot (356). Therefore, longitudinal translation of outer tube (352) rotates the first portion of clamp arm (382) about the second portion of clamp arm (382). Thus, as can be seen in the transition from FIG. 11A to FIG. 11B, tubes (352, 370) cooperate to pivot clamp arm (382) toward blade (390) when outer tube (352) is retracted proximally relative to inner tube (370). It should be understood that clamp arm (382) may be pivoted back away from blade (390) (e.g., from the position shown in FIG. 11B to the position shown in FIG. 11A) by translating outer tube (352) distally relative to inner tube (370), in reverse of the operation shown in FIGS. 11A-11B. In an exemplary use, clamp arm (382) may be pivoted toward blade (390) to grasp, compress, seal, and sever tissue captured between clamp pad (382) and blade (390). Clamp arm (382) may be pivoted away from blade (390) to release tissue from between clamp pad (382) and blade (390); and/or to perform blunt dissection of tissue engaging opposing outer surface of clamp arm (382) and blade (390).

While inner tube (170) includes distally projecting tongue (172), inner tube (370) of the present example includes a pair of angled distal prongs (372) defining a longitudinal channel (374). Angled distal prongs (372) each have a flat surface (378) extending from prongs (372). Together, each angled distal prong (372) and corresponding flat surface (378) define a pin hole (376). As will be described in greater detail below, pin holes (376) are dimensioned to receive integral pins (388) of clamp arm (382). As also seen in FIGS. 11A-12E, a tab (360) is integrally fixed on one angled distal prong (372), and extends across longitudinal channel (375) above the other angled distal prong (372).

Figure 12A:
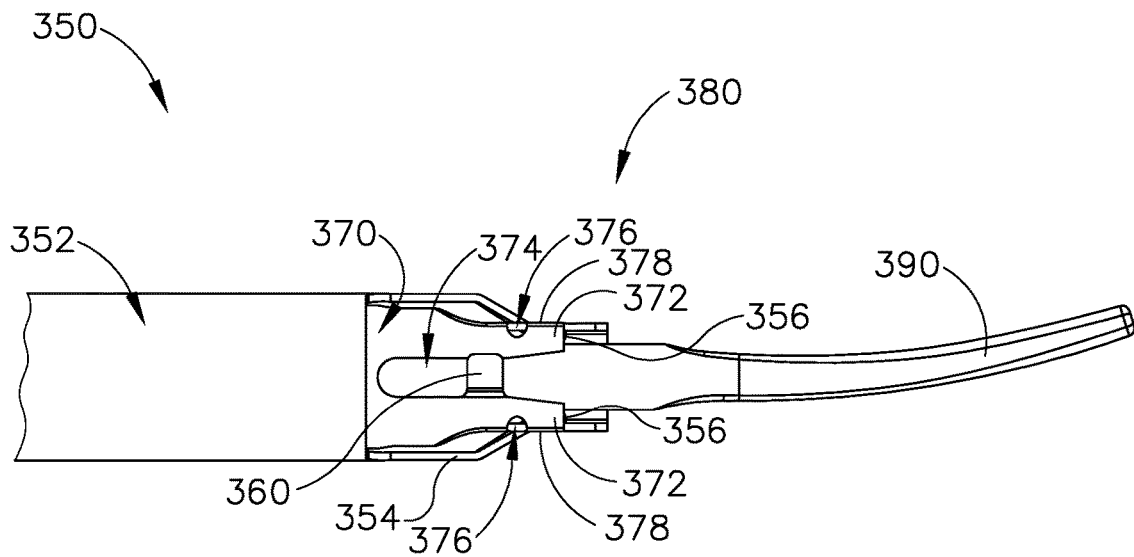
FIG. 12A depicts a top elevational view of the end effector and shaft assembly of FIG. 11A, where the clamp arm is detached from the inner and outer tube.
Figure 12B:
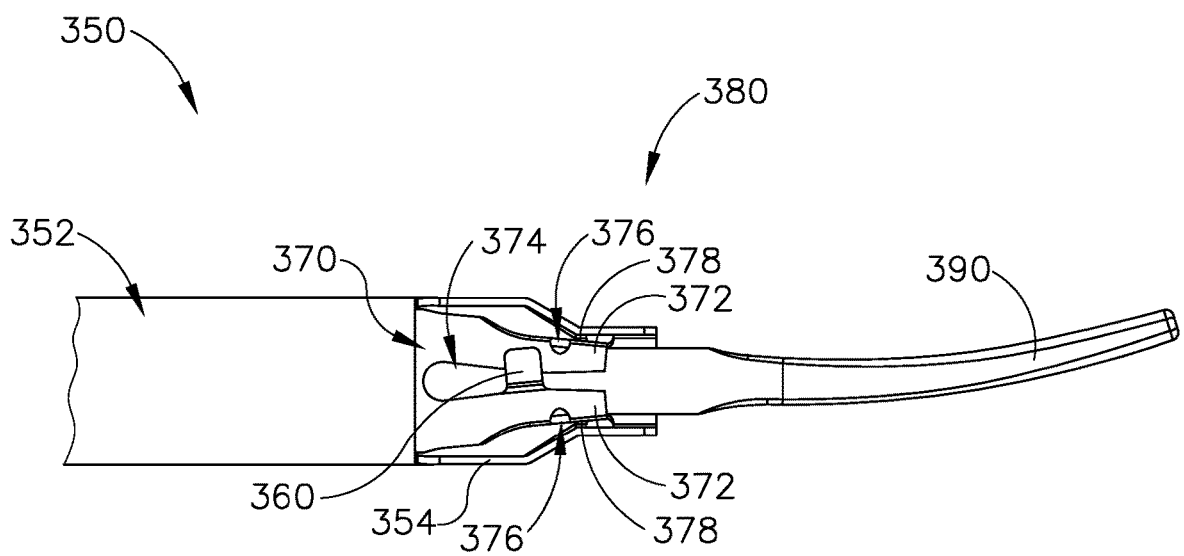
FIG. 12B depicts a top elevational view of the end effector and shaft assembly of FIG. 11A, where the clamp arm is detached from the inner and outer tube, where the distal prongs of the inner tube are pressed toward each other.
Figure 12C:
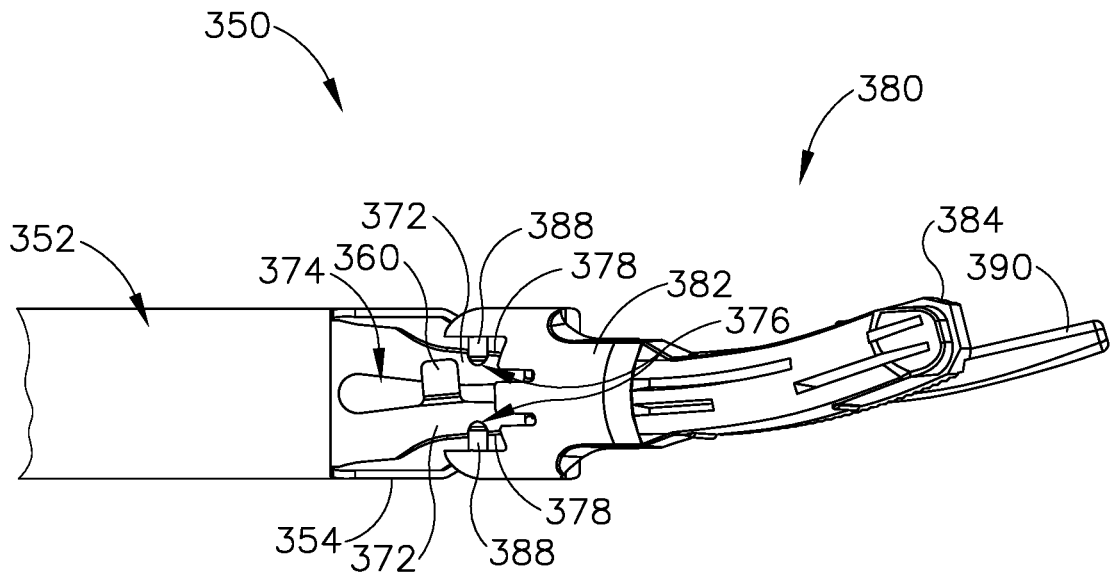
FIG. 12C depicts a top elevational view of the end effector and shaft assembly of FIG. 11A, where the clamp arm is in the open position and attached to the inner and outer tube, where the distal prongs of the inner tube are pressed toward each other.

FIGS. 12A-12E show an exemplary assembly of clamp arm (382) and inner tube (370). FIG. 12A shows shaft assembly (350) and end effector (380) without clamp arm (382) attached. Similar to clamp arm (282) in FIG. 10A, clamp arm (382) may be placed over angled distal prongs (372) such that integral pins (388) are laterally aligned with angled distal prongs (372). It should be understood that inner tube (370) is made out of a resilient material, such that angled distal prongs (372) may flex relative to one another within longitudinal channel (374). Therefore, as seen in FIG. 12B, an operator may pinch angled distal prongs (372) or flats (378) together, such that angled distal prongs (372) flex toward each other within longitudinal channel (374). As seen in FIG. 12C, angled distal prongs (372) are then spaced such that integral pins (388) may slide within pin holes (376) and abut against the portion of pin holes (376) defined by flats (378). At this stage, integral pins (388) are within pin holes (376).

Figure 12D:
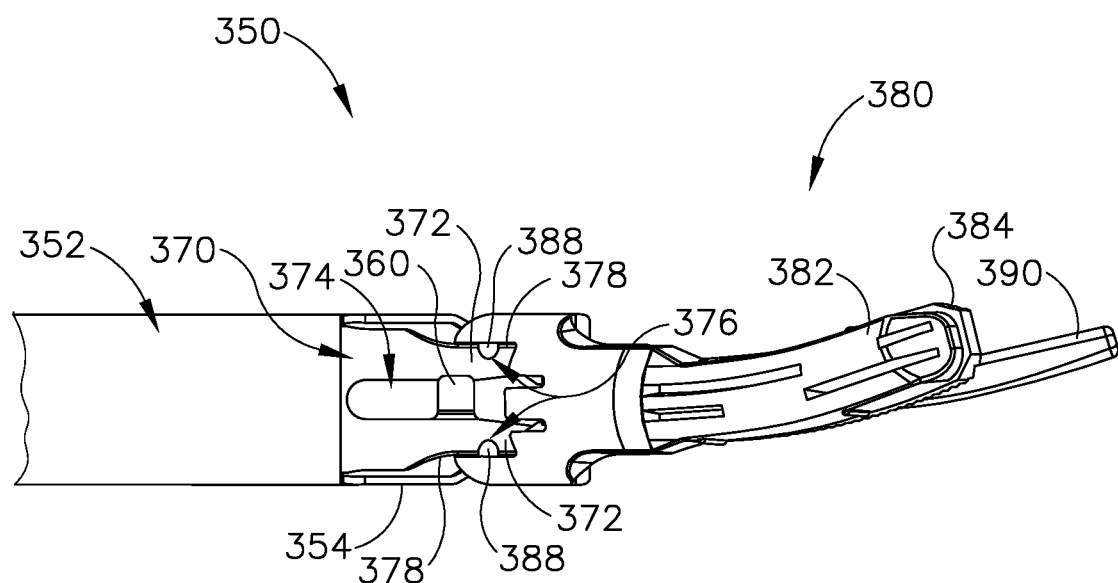
FIG. 12D depicts a top elevational view of the end effector and shaft assembly of FIG. 11A, where the clamp arm is in the open position and attached to the inner and outer tube, where the distal prongs of the inner tube engage the integral pins of the clamp arm.
Figure 12E:
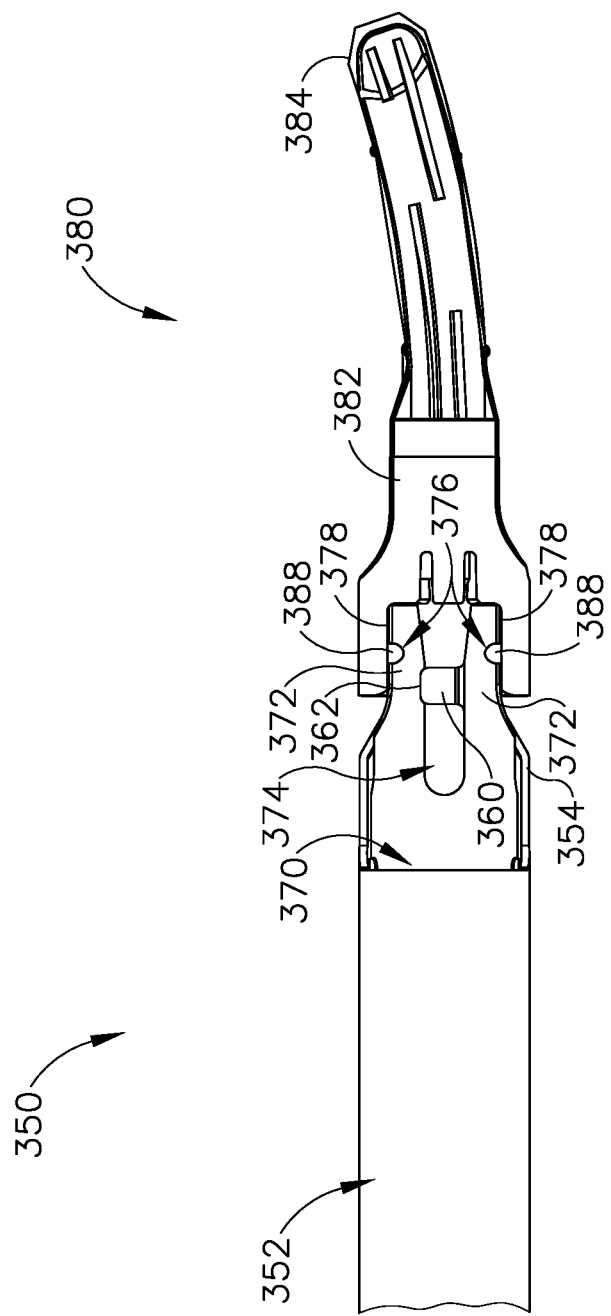
FIG. 12E depicts a top elevational view of the end effector and shaft assembly of FIG. 11A, where the clamp arm is in the closed position and attached to the inner and outer tube.

With integral pins (388) are within pin holes (376), and as seen in FIG. 12D, the operator may now release angled distal prongs (372) and/or flats (378). Due to the resilient nature of angled distal prongs (372) and flats (378), both angled distal prongs (372) and flats (378) return to their natural position, as shown in FIG. 12D. Additionally, integral pins (388) abut against both angled distal prongs (372) and flats (378). Integral pins (388) are now fixed within pin holes (376) at this stage. With pins (388) fixed within pin holes (376), and as shown in FIG. 12E, the operator may fix or secure tab (360) to the other angled distal prong (372) that tab (360) is not already integrally fixed to. End (362) of tab (360) may be fixed to the other angled distal prong (372) through welding or any other suitable method known to one having ordinary skill in the art in view of the teachings herein. With tab (360) fixed to both angled distal prongs (372), angled distal prongs (372) and/or flats (378) are no longer capable of deflecting inwardly toward one another to release integral pins (388) from pin holes (376). It should be understood that integral pins (388) do not extend laterally across the width of inner tube (370). Additionally, integral pins (388) are dimensioned to not extend across the lateral width of blade (390). Therefore, chances of blade (390) making contact with integral pins (388) are reduced or eliminated.

While in the current example, a user flexes angled distal prongs (372) and/or flats (378) towards one another in the present example, it should be understood that this is merely optional. In some alternative versions, the operator may force integral pins (388) on top of angled distal prongs (372), and contact between integral pins (388) and angled distal prongs (372) may provide a camming action that flexes angled distal prongs (372) and flats (378) toward each other. In some such versions, integral pins (388) may have angled surfaces that cooperate with angled distal prongs (372) to further promote this camming action. Other ways that angled distal prongs (373) and flats (378) may flex toward each other to create the appropriate gap for insertion of integral pins (388) into pin holes (376) will be apparent to one having ordinary skill in the art in view of the teachings herein.

C. Removable Retention Cap

FIGS. 13A-14C show another alternative shaft assembly (450) and alternative end effector (480) that may be readily incorporated into instrument (10) described above in place of shaft assembly (150) end effector (180). End effector (480) includes a clamp arm (482) and clamp pad (484) that are substantially similar to clamp arm (282) and clamp pad (284) described above, with difference described in detail below. As best seen in FIG. 14A, shaft assembly (450) includes an outer tube (452), an inner tube (470), and an acoustic waveguide (492) extending through both outer tube (452) and inner tube (470). Outer tube (452), inner tube (470), and acoustic waveguide (492) are substantially similar to outer tube (252), inner tube (270), and acoustic waveguide (292) mentioned above, respectively, with differences described below.

Figure 13A:
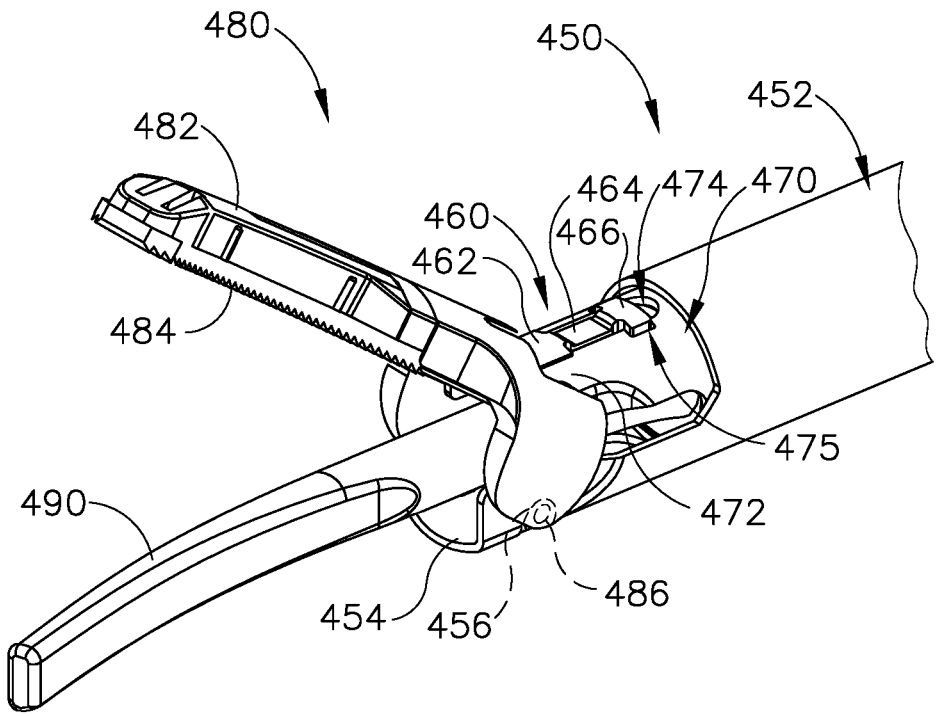
FIG. 13A depicts a perspective view of another alternative end effector and alternative shaft assembly that may be readily incorporated into the instrument of FIG. 1, where the end effector is in the open position.
Figure 13B:
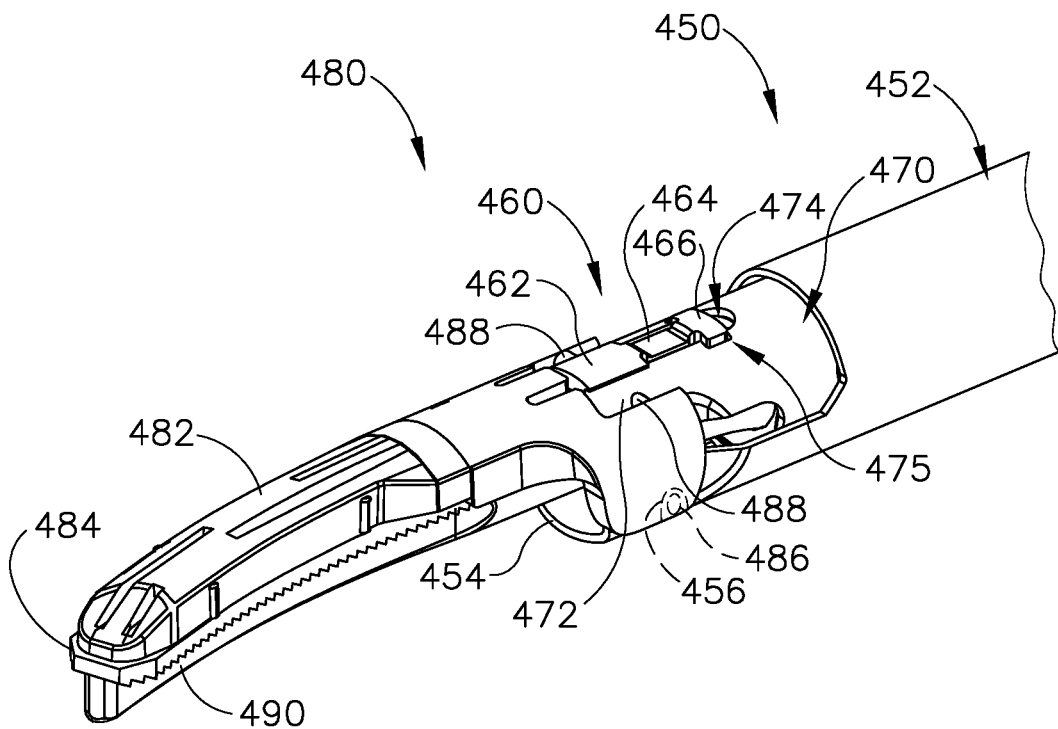
FIG. 13B depicts a perspective view of the end effector and shaft assembly of FIG. 13A, where the end effector is in the closed position.

As best seen in FIGS. 13A-13B, outer tube (452) is operable to translate longitudinally relative to inner tube (470) to selectively pivot clamp arm (482) toward and away from blade (490). To accomplish this, integral pin features (486) of clamp arm (482), which are substantially similar to integral pin features (286) mentioned above, pivotally secure a first portion of clamp arm (482) to pin slot (456) of a distally projecting tongue (454) of outer tube (452); while integral pin features (488) pivotally secure a second portion of clamp arm (482) to angled distal prongs (472) of inner tube (470) via pin holes (476). It should be understood that integral pin features (486) may vertically translate within pin slot (456). Therefore, longitudinal translation of outer tube (452) rotates the first portion of clamp arm (482) about the second portion of clamp arm (482). Thus, as can be seen in the transition from FIG. 13A to FIG. 13B, tubes (452, 470) cooperate to pivot clamp arm (482) toward blade (490) when outer tube (452) is retracted proximally relative to inner tube (470). It should be understood that clamp arm (482) may be pivoted back away from blade (490) (e.g., from the position shown in FIG. 13B to the position shown in FIG. 13A) by translating outer tube (452) distally relative to inner tube (470), in reverse of the operation shown in FIGS. 13A-13B. In an exemplary use, clamp arm (482) may be pivoted toward blade (490) to grasp, compress, seal, and sever tissue captured between clamp pad (482) and blade (490). Clamp arm (482) may be pivoted away from blade (490) to release tissue from between clamp pad (482) and blade (490); and/or to perform blunt dissection of tissue engaging opposing outer surface of clamp arm (482) and blade (490).

Similar to inner tube (270), inner tube (470) of the present example includes a pair of angled distal prongs (472) defining a longitudinal channel (474). Angled distal prongs (472) each have a flat surface (478) extending from prongs (472). Together, each angled distal prong (472) and corresponding flat surface (478) define a pin hole (476). Clamp arm (482) may be attached to inner tube (470) in substantially the same manner as described above for coupling clamp arm (282) with inner tube (270), with the difference of inserting removable cap (460) as will be describe below. It should therefore be understood that inner tube (470) is made out of a resilient material, such that angled distal prongs (472) may flex relative to one another within longitudinal channel (474). Pin holes (476) are dimensioned to receive integral pins (488) of clamp arm (482) when angled distal prongs (472) and flats (478) are flexed toward each other within longitudinal channel (474). With integral pins (488) inserted into pin holes (476), angled distal prongs (472) and flats (478) may return to their natural position such that integral pins (488) abut against portions of angled distal prongs (472) and flats (478) defining pin holes (476).

Figure 14A:
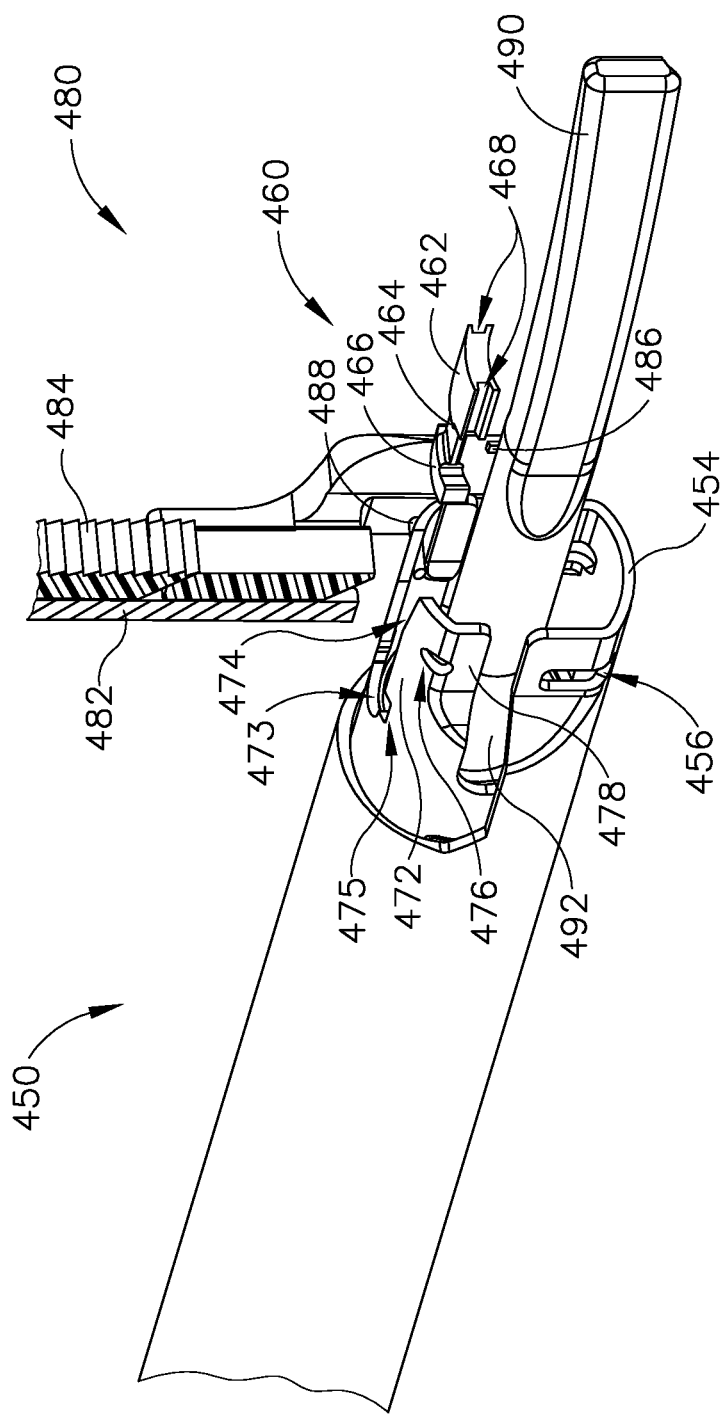
FIG. 14A depicts a partial cross-sectional perspective view of the end effector and shaft assembly of FIG. 13A, where the end effector is in the open position, where the removable clip is removed from the distal prongs of the inner tube.
Figure 14B:
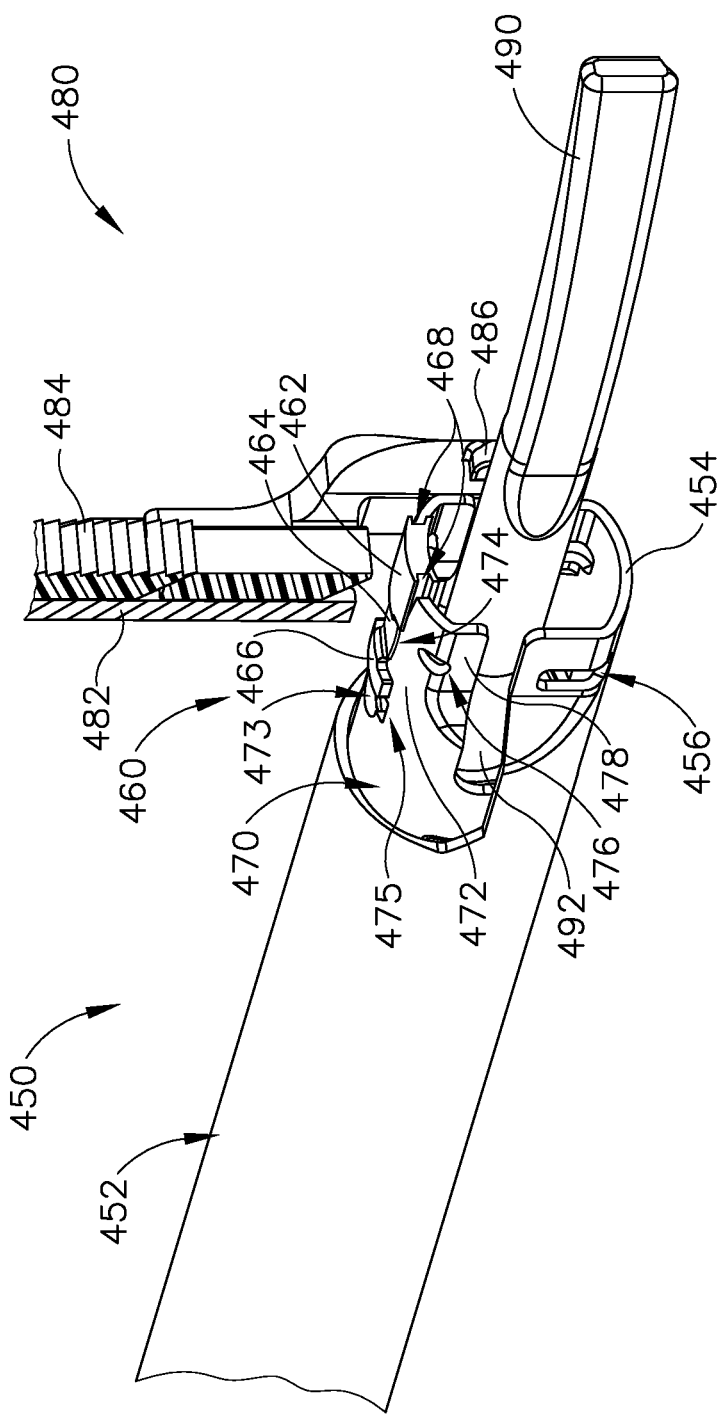
FIG. 14B depicts a partial cross-sectional perspective view of the end effector and shaft assembly of FIG. 13A, where the end effector is in the open position, where the removable clip is partially inserted in between the distal prongs of the inner tube.
Figure 14C:
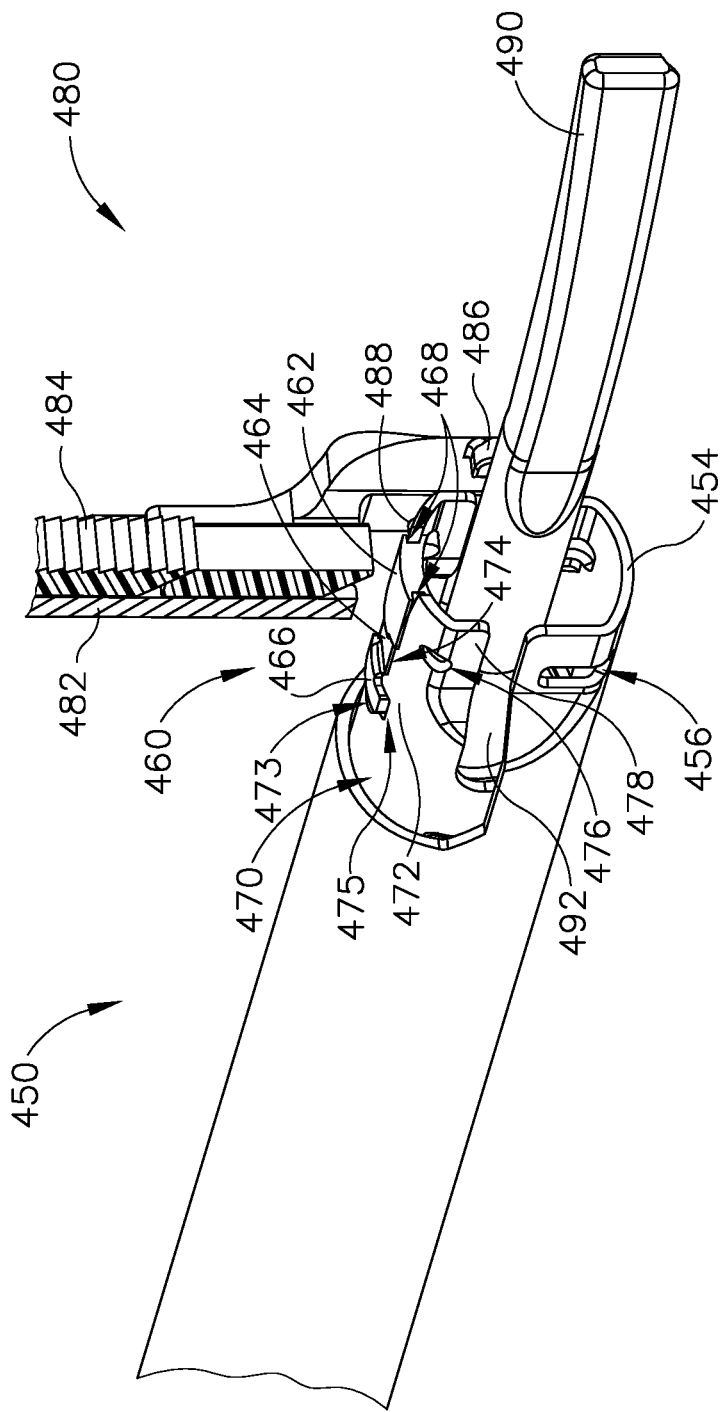
FIG. 14C depicts a partial cross-sectional perspective view of the end effector and shaft assembly of FIG. 13A, where the end effector is in the open position, where the removable clip is completely inserted in between the distal prongs of the inner tube.

When pins (488) are disposed in corresponding pin holes (476), and as best seen in FIGS. 14A-14C, removable cap (460) may be inserted into longitudinal channel (474) to prevent angled distal prongs (472) and/or flats (478) from deflecting inwardly toward one another to release integral pins (488) from pin holes (476). Removable cap (460) includes a spacer portion (462), a resilient portion (464) extending from spacer portion (462), and a tab (466) extending from resilient portion (464). Additionally, longitudinal channel (474) includes an access channel (473) and a locking channel (475). Access channel (473) is sized so an operator may insert an object or their finger within access channel (473) to selectively remove removable cap (460) by sliding removable cap (460) distally. Locking channel (475) is sized to receive tab (466) when removable cap (460) is fully inserted, thereby longitudinally locking removable cap (460) relative to inner tube (470).

Spacer portion (462) defines a pair of longitudinal slots (468). Longitudinal slots (468) are sized to receive the inner edges of angled distal prongs (472) when removable cap (460) is installed. As best seen in FIGS. 14A-14B, the operator may vertically align longitudinal slots (468) with the edges of angled distal prongs (472) so that longitudinal slots (468) house the edges of angled distal prongs (472). Resilient member is capable of bending, such that tab (466) may vertically move relative to spacer portion (462). Thus, as shown in FIG. 14B, when spacer portion (468) initially engages angled distal prongs (472), tab (466) may slide on top of longitudinal channel (474) and angled distal prongs (472).

As best seen in FIG. 14C, when spacer portion (462) slides a sufficient distance proximally toward inner tube (470), tab (466) may fit within locking channel (475). With tab (466) no longer forced above longitudinal channel (464) through engagement with angled distal prongs (472), the resilient nature of resilient portion (464) moves tab (466) within locking channel (475). Tab (466) is thereby vertically aligned with spacer portion (462) at this stage. As described above, spacer portion (462) is located between angled distal prongs (472) such that angled distal prongs (472) and/or flats (478) are no longer capable of deflecting inwardly toward one another to release integral pins (488) from pin holes (476). Additionally, tab (466) resting within locking channel (475) prevents unintentional longitudinal movement of removable cap (460) relative to inner tube (470). If an operator desires to remove removable cap (460) (e.g. to remove clamp arm (482)), the operator may push tab (466) downwardly so tab (466) no longer engages locking channel (475), then slide removable cap (460) in the distal direction. Alternatively, an operator user may insert an object or their finger into access channel (473) in order to lift tab (466) above locking channel (475), then slide removable cap (460) in the distal direction.

III. Exemplary Locking and Location Features For a Removable Blade

In some instances, ultrasonic blade (190, 290, 390, 490) and waveguide (192, 292, 392, 492) may be removable from the rest of shaft assembly (150, 250, 350, 450) and end effector (180, 280, 380, 480). This may enable cleaning and/or other processing of ultrasonic blade (190, 290, 390, 490) and waveguide (192, 292, 392, 492). In such cases, it may be desirable to have a locking and locating feature associated with instrument (10) such that ultrasonic blade (190, 290, 390, 490) and waveguide (192, 292, 393, 492) are oriented in the same angular position relative to shaft assembly (150, 250, 350, 450) and end effector (180, 280, 380, 480) every time a user reassembles ultrasonic blade (190, 290, 390, 490) and waveguide (192, 292, 392, 492) within end effector (180, 280, 380, 480) and shaft assembly (150, 250, 350, 450). This consistency in the angular orientation of ultrasonic blade (190, 290, 390, 490) and waveguide (192, 292, 393, 492) may be desirable in order to ensure that the proper region of ultrasonic blade (190, 290, 390, 490) is facing clamp pad (184, 284, 384, 484). Having consistency in the angular orientation of ultrasonic blade (190, 290, 390, 490) and waveguide (192, 292, 393, 492) may also be particularly desirable in contexts where ultrasonic blade (190, 290, 390, 490) extends along a curve, to ensure that the curve of a complimentarily curved clamp arm (182, 282, 382, 482) is aligned with the curve of ultrasonic blade (190, 290, 390, 490).

The following examples provide various features that may be used to provide consistent angular orientation of ultrasonic blade (190, 290, 390, 490) as ultrasonic blade (190, 290, 390, 490) and waveguide (192, 292, 393, 492) are inserted into shaft assembly (150, 250, 350, 450). Further examples are described in U.S. patent application Ser. No. 14/868,574, entitled "Ultrasonic Surgical Instrument with Removable Handle Assembly," filed Sep. 29, 2015, published as U.S. Pub. No. 2016/0015419 on Jan. 21, 2016, issued as U.S. Pat. No. 10,349,967 on Jul. 16, 2019, the disclosure of which is incorporated by reference herein. It should be understood that the teachings below may be readily combined with any of the teachings above, such that the examples below are not intended to be exclusive of the examples above. It should also be understood that the teachings below may be readily applied to other versions of instrument (10), not just the versions of instrument (10) that are described herein.

A. Spring Loaded Key Lock

Figure 15A:
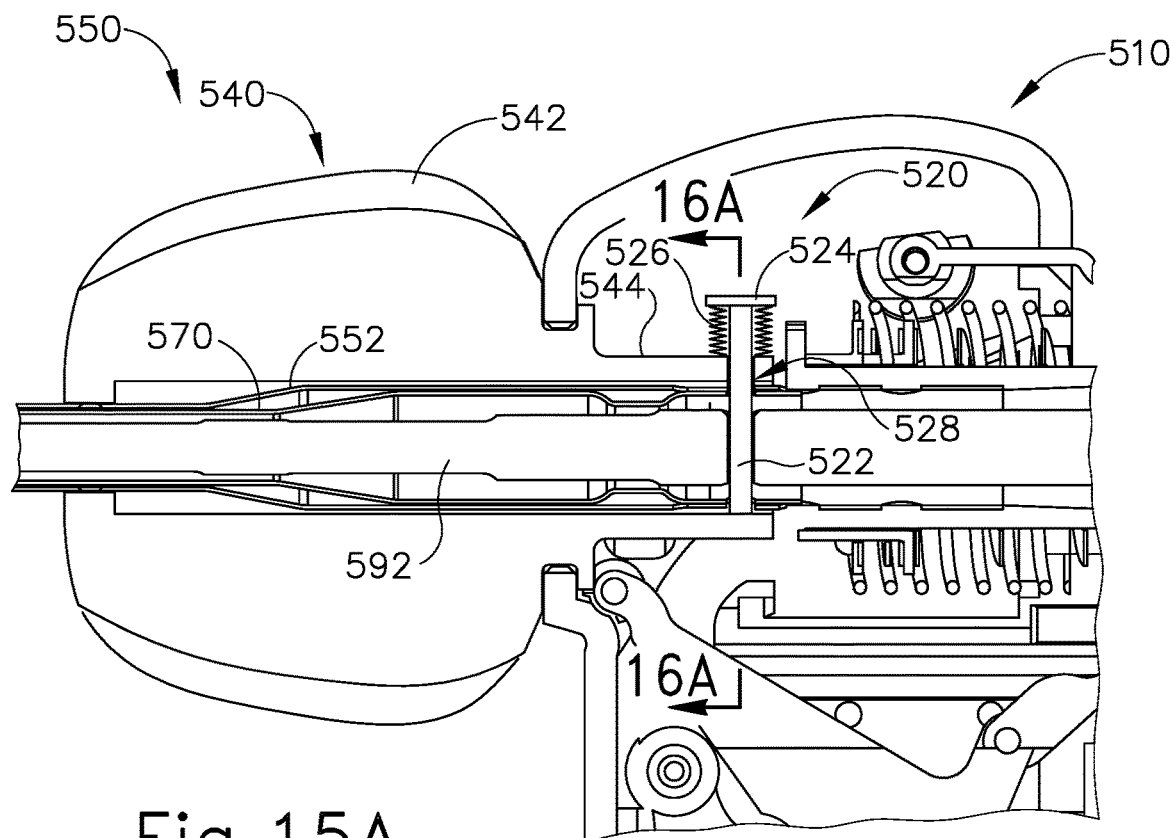
FIG. 15A depicts a side cross-sectional view of an alternative shaft assembly that may be readily incorporated into the instrument of FIG. 1, where a spring loaded key lock is in a closed position.
Figure 15B:
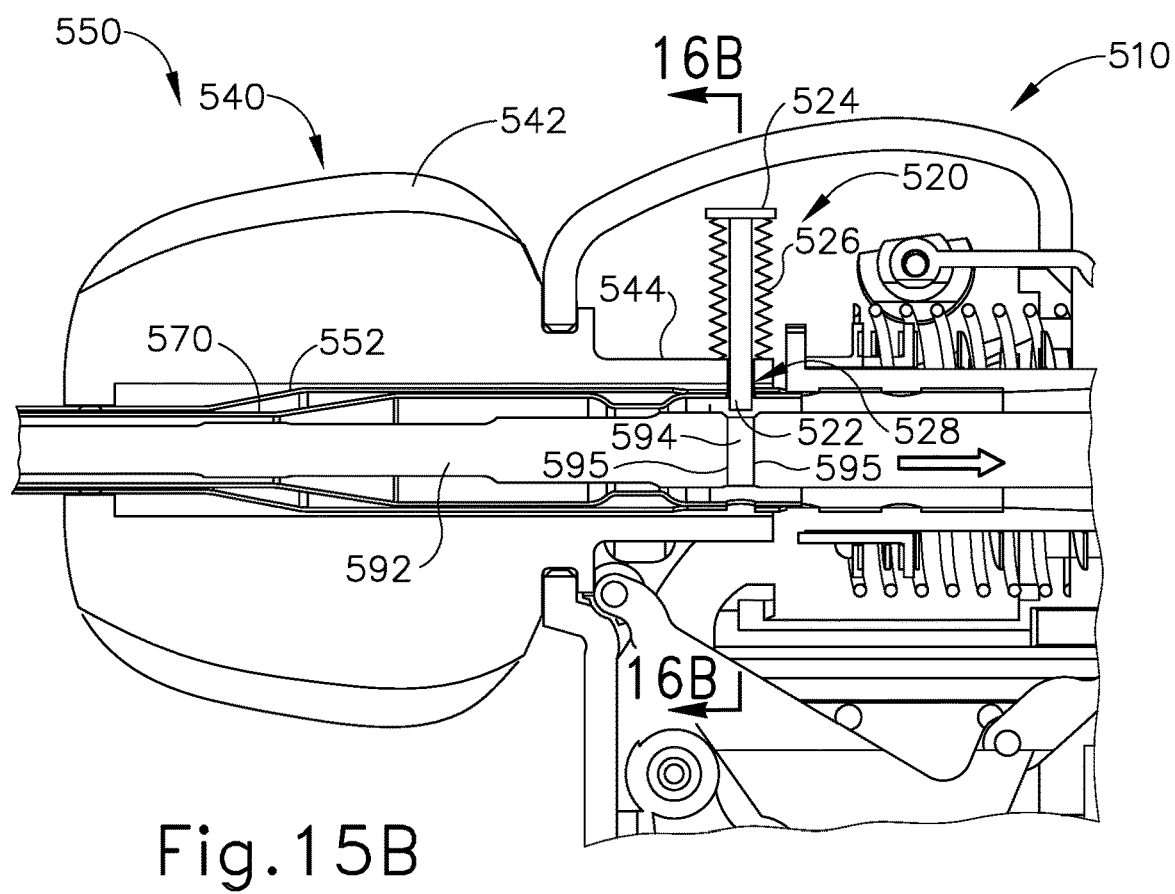
FIG. 15B depicts a side cross-sectional view of the shaft assembly of FIG. 15A, where the spring loaded key lock is in an open position.

FIGS. 15A-15B show an alternative shaft assembly (550) and an alternative body portion (510) that may be readily incorporated into instrument (10) described above. Shaft assembly (550) includes a rotation assembly (540) that is operable to rotate shaft assembly (550) relative to body portion (510). Rotation assembly (540) includes a rotation knob (542) unitarily attached to a sleeve (544) extending into body portion (510). Shaft assembly further includes an outer tube (552), an inner tube (570), and a waveguide (592) extending through inner tube (570) and outer tube (552). Outer tube (552), inner tube (570) and waveguide (592) are substantially similar to outer tube (152), inner tube (170), and waveguide (192) described above, respectively, with differences described below. As best seen in FIGS. 15A-15B, a portion of outer tube (552), inner tube (570) and waveguide (592) extend through rotation knob (542) and sleeve (544).

Body portion (510) also houses a spring loaded key lock assembly (520). As will be described in greater detail below, spring loaded key lock assembly (520) is capable of selectively locking the longitudinal position of waveguide (592) relative to inner tube (570). Additionally, as will be described in greater detail below, spring loaded key lock assembly (520) is also capable of unlocking waveguide (592) relative to inner tube (570) and outer tube (552), such that waveguide (592) may be removed from body portion (510) for cleaning or other reasons.

Spring loaded key lock (520) includes a handle (524) that is connected to a pair of locking forks (522). Lock (520) further includes a biasing member (526) that is fixed to sleeve (544) of rotation assembly (540) and handle (524). Locking forks (522) extend from handle (524) toward sleeve (544). As best seen in FIG. 15A, biasing member (526) biases handle (524) toward sleeve (544). However, as best seen in FIG. 15B, an operator may pull handle (524) away from sleeve (544) to stretch biasing member (526). However, as soon as a user releases handle (524), biasing member (526) will resiliently actuate handle (525) toward sleeve (544).

Figure 16A:
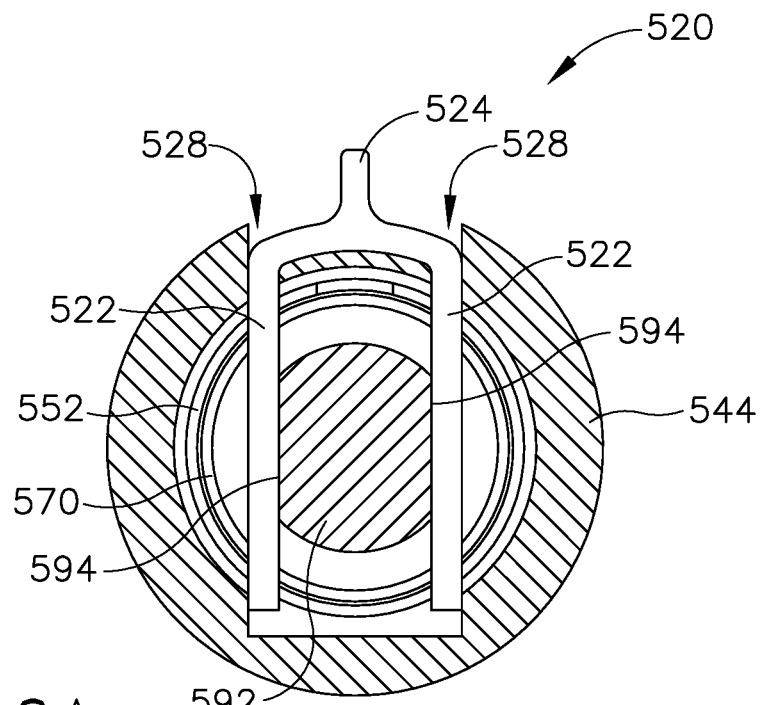
FIG. 16A depicts a cross-sectional view of the shaft assembly of FIG. 15A, taken along line 16A-16A of FIG. 15A, where the spring loaded key lock is in the closed position.
Figure 16B:
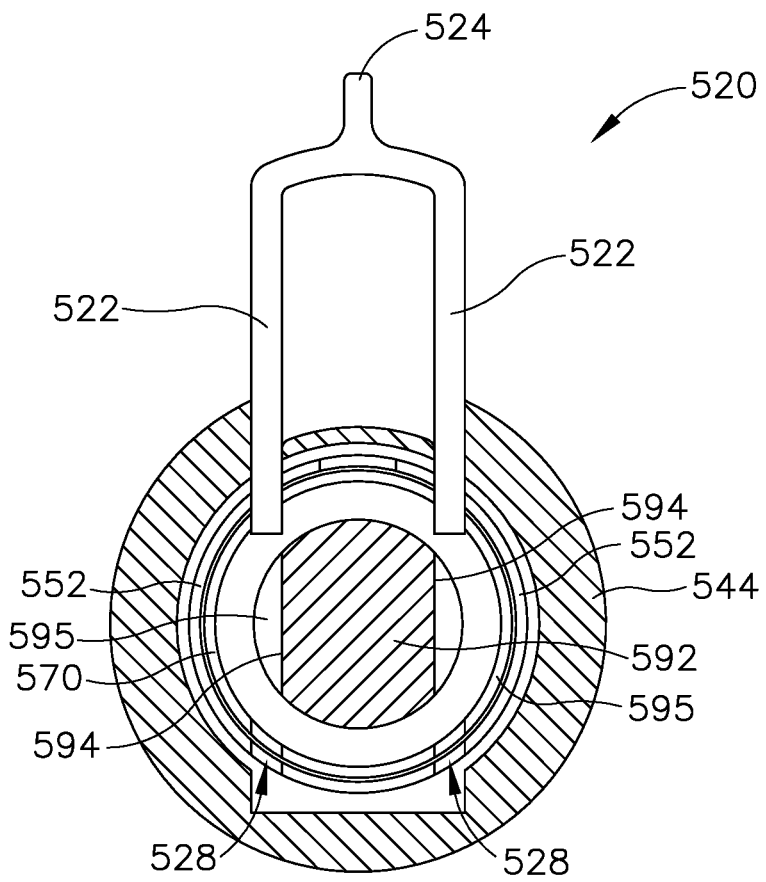
FIG. 16B depicts a cross-sectional view of the shaft assembly of FIG. 15A, taken along line 16B-16B of FIG. 15B, where the spring loaded key lock is in the open position.

As can be seen in FIGS. 16A-16B, sleeve (544), outer tube (552), and inner tube (570) define a pair of key slots (528) that are dimensioned to receive locking forks (522). Locking forks (522) may also actuate within key slots (528). Additionally, waveguide (592) defines a pair of keyed flats (594) and a pair of faces (595). Faces (595) are adjacent and perpendicular to keyed flats (594). As best seen in FIGS.15A-15B, keyed flats (594) are dimensioned with a substantially similar, if not exact, width of locking forks (522). Therefore, when key lock assembly (520) engages waveguide (592), faces (595) prevent waveguide (592) from traveling in the longitudinal direction due to interaction of faces (595) and locking forks (522). Additionally, as best seen in FIG. 16A, locking forks (522) are spaced apart from one another so that each locking fork (522) makes contact with its respective keyed flat (594) when locking forks (522) are located within keyed slots (528). Therefore, keyed flats (594) prevent waveguide (592) from lateral movement or rotating about its own longitudinal axis due to interaction of keyed flats (594) and locking forks (522).

Additionally, as best seen in FIG. 15B and FIG. 16B, an operator may pull handle (524) away from sleeve (544) so that locking forks (522) travel along key slots (528). Locking forks (522) may travel along key slots (528) until locking forks (522) no longer make contact with faces (595) or keyed flats (594). An operator may thus pull waveguide (592) in the proximal direction until waveguide (592) is sufficiently removed from inner tube (570) and outer tube (552). If the operator desires to place waveguide (592) back into inner tube (570) and outer tube (552), the operator may pull handle (524) away from sleeve (544), insert waveguide (592) into inner tube (570) and outer tube (552) until locking forks (522) align with keyed flats (594), and then allow biasing member (526) to force locking forks (522) within key slots (528).

B. Inner and Outer Tube With Orientation Features

Figure 17:
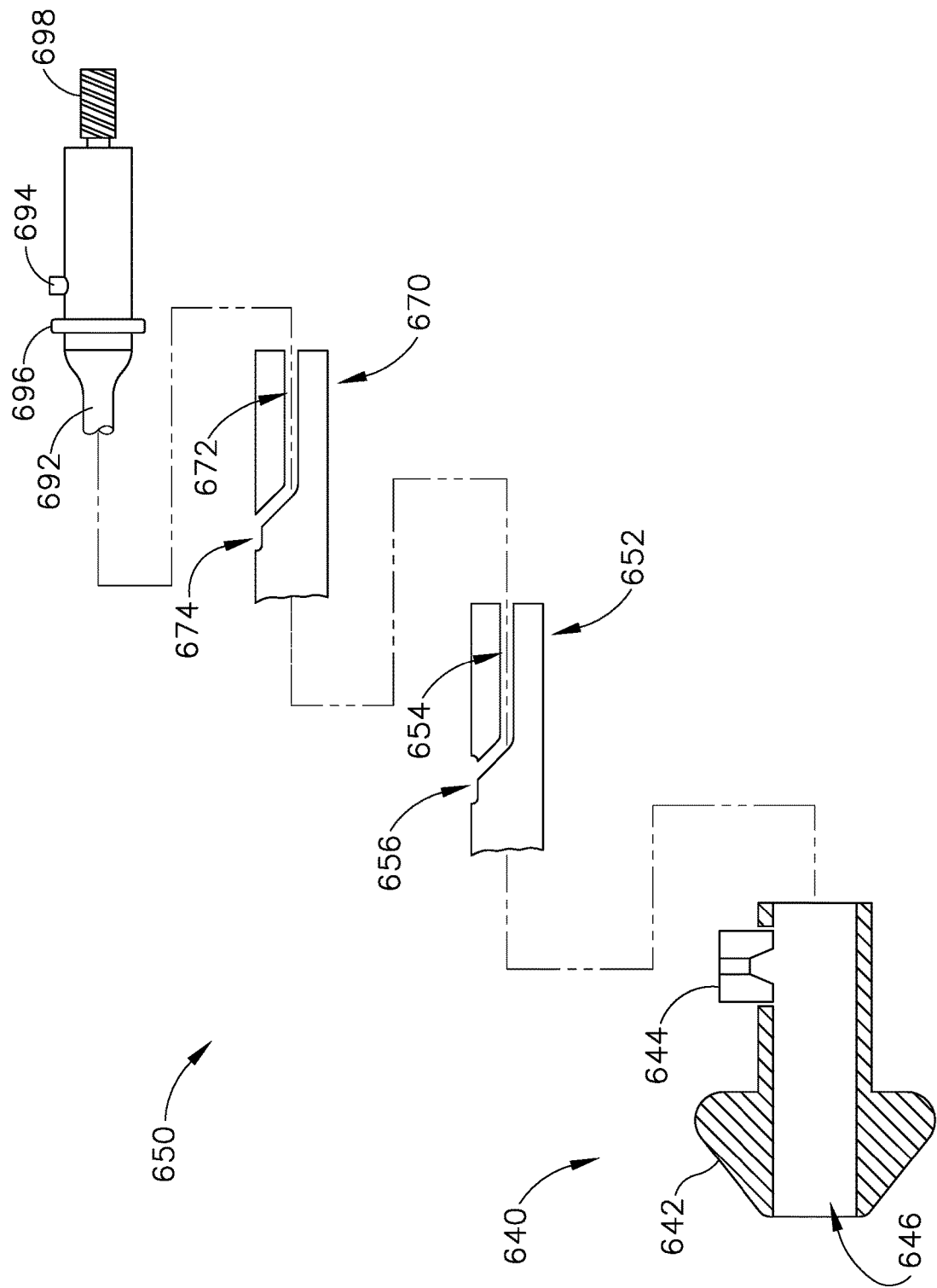
FIG. 17 depicts an exploded side view of another alternative shaft assembly that may be readily incorporated into the instrument of FIG. 1.
Figure 18A:
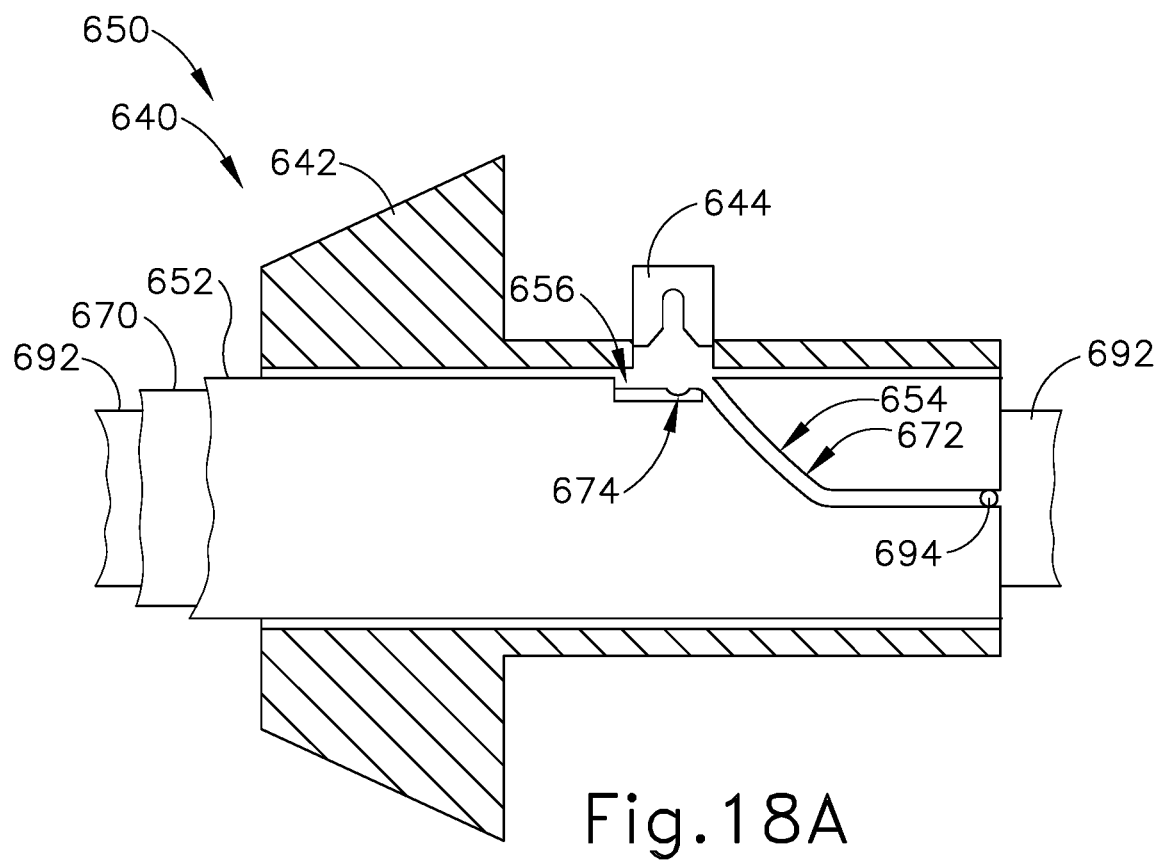
FIG. 18A depicts a partial side cross-sectional view of the shaft assembly of FIG. 17, where the waveguide is in a proximal position.
Figure 18B:
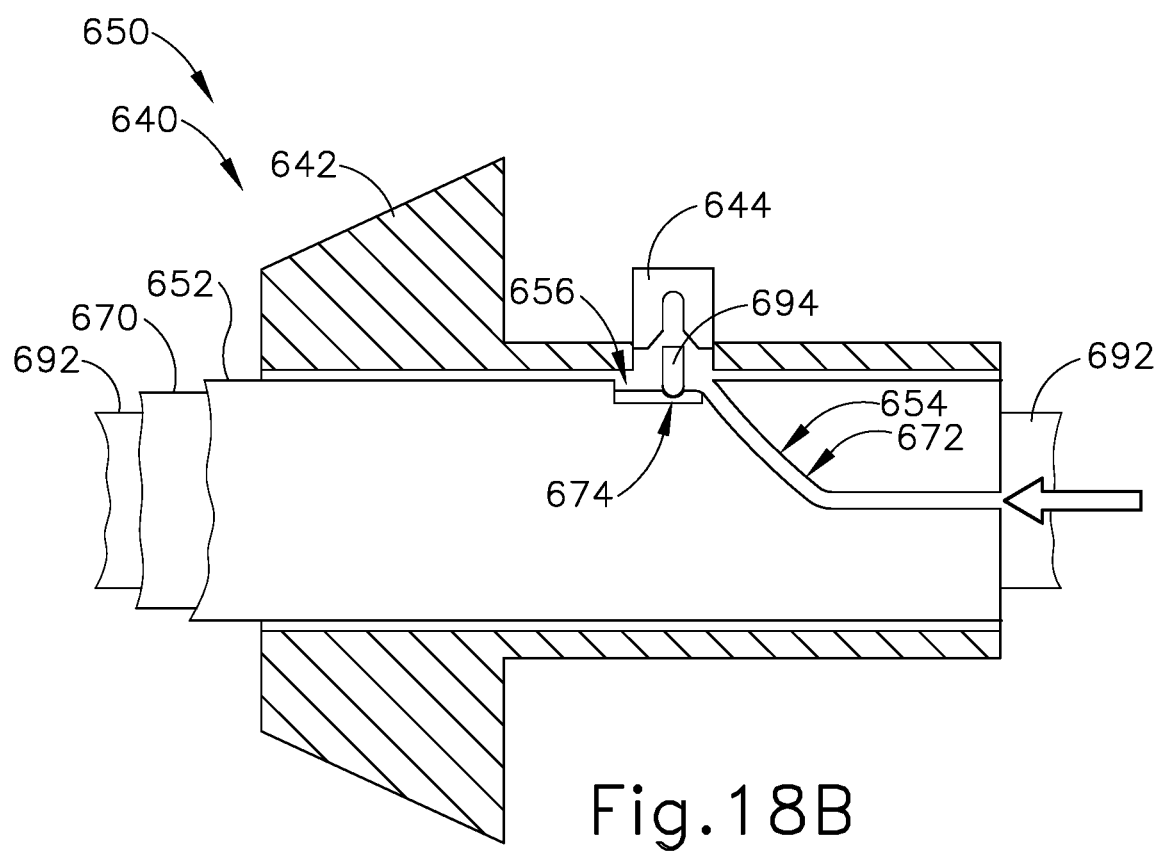
FIG. 18B depicts a partial side cross-sectional view of the shaft assembly of FIG. 17, where the waveguide is in a distal position.
Figure 18C:
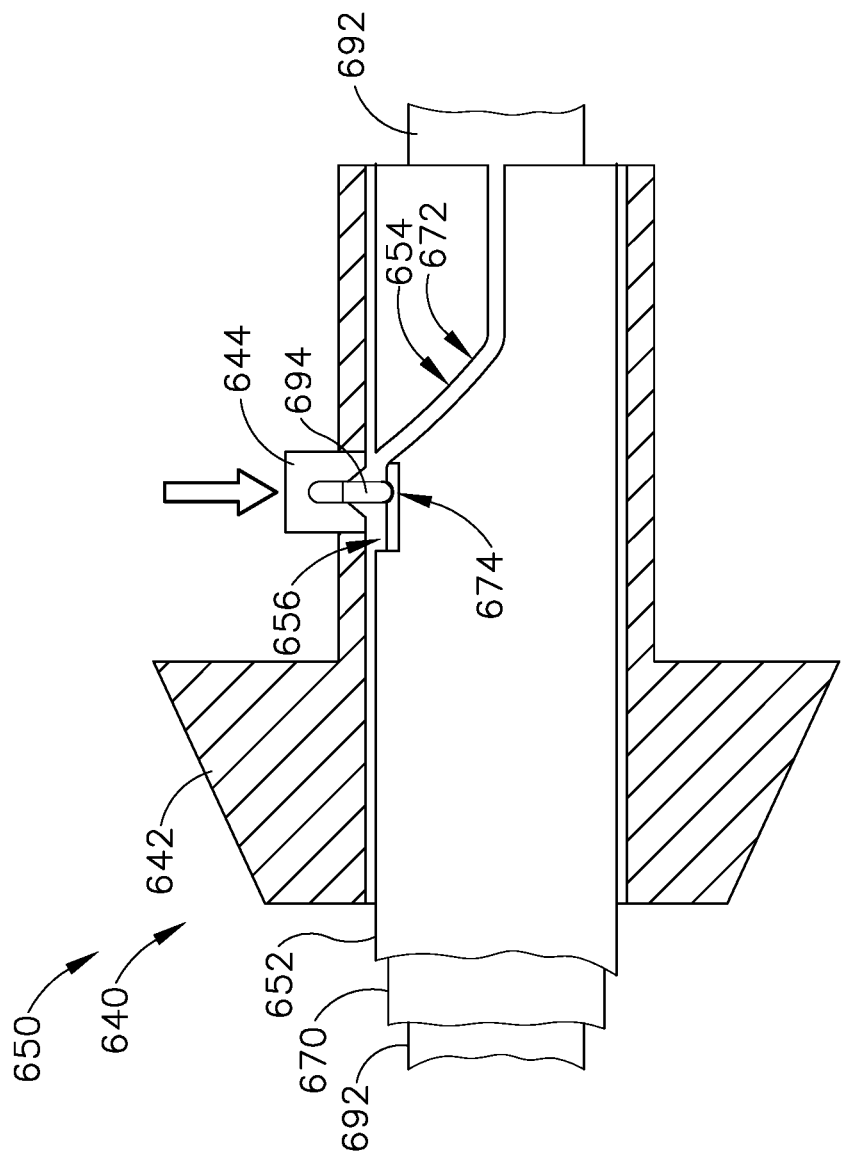
FIG. 18C depicts a partial side cross-sectional view of the shaft assembly of FIG. 17, where the waveguide is in the distal position and locked relative to the rotation assembly.

FIGS. 17-18C show another alternative shaft assembly (650) that may be readily incorporated into instrument (10) described above. Shaft assembly (650) includes an ultrasonic waveguide (692), an inner tube (670), an outer tube (652), and a rotation assembly (640); which are substantially similar to ultrasonic waveguide (192), inner tube (170), outer tube (152), and rotation assembly (540), respectively, except for the differences described below.

As best seen in FIG. 17, ultrasonic waveguide (692) includes a seal (696), a cam pin (694) and a threaded stud (698) that is configured to couple with an ultrasonic transducer (not shown). Inner tube (670) includes a cam slot (672) extending from the proximal end of inner tube (670) and terminating at a placement hole (674). Outer tube (652) includes a cam slot (654) extending from the proximal end of outer tube (652) and terminating in a translation slot (656). Rotation assembly (640) includes a rotation knob (642) defining a channel (646) and a locking feature (644). Locking feature (644) may actuate relative to the rest of rotation assembly (640). It should be understood that cam pin (694) may fit within both cam slots (672, 654) and radially extend from the rest of ultrasonic waveguide (692) as to extend beyond the dimensions of inner tube (670) and outer tube (652).

FIGS. 18A-18C show how waveguide (692) may be assembled within outer tube (652), inner tube (670), and rotation knob (642). Outer tube (652) and inner tube (670) are partially disposed within channel (646) of rotation knob (642). An operator may insert the distal end of waveguide (692) into the proximal openings of inner tube (670) and outer tube (552) such that cam pin (694) is aligned with cam slots (672, 654). As mentioned above, camp pin (694) extends radially outwardly from the rest of ultrasonic waveguide (692) such that cam pin (694) extends beyond the dimensions of inner tube (670) and outer tube (652). Therefore, when cam pin (694) is aligned with cam slots (672, 654), cam pin (694) extends through inner tube (670) and outer tube (652) via cam slots (672, 654). It should be understood that cam slots (672, 654) are aligned when outer tube (652) is actuated to its most distal position relative to inner tube (670). However, cam slots (672, 654) may be dimensioned to align at any other longitudinal location of outer tube (652) relative to inner tube (670) as would be apparent to one having ordinary skill in the art in view of the teachings herein.

As shown in FIG. 18B, the operator push ultrasonic waveguide (692) in the distal direction. As waveguide (692) travels distally, cam slots (672, 654) force waveguide (692) to rotate via cam pin (694). Waveguide (692) may travel distally within inner tube (670) and outer tube (652) until cam pin (694) reaches placement hole (674) as shown in FIG. 18B. Because cam pin (694) is located at the same location relative to the rest of waveguide (692), and because cam slots (672, 654) are located at the same location when aligned, waveguide (692) will uniformly locate in the same longitudinal and rotational position every time waveguide (692) is inserted into inner tube (670) and outer tube (652). Placement hole (674) is located directly adjacent to locking feature (644). As described above, locking feature (644) is capable of actuating relative to the rest of rotation assembly (640). Additionally, locking feature (644) is dimensioned for a snap fit with cam pin (694) when locking feature (644) is actuated toward cam pin (694) as shown in FIG. 18C. Waveguide (692) is thereby rotationally and longitudinally fixed relative to rotation assembly (640). While locking feature (644) uses a snap fit to lock with cam pin (694) in the current example, any other suitable method of fixing cam pin (694) to locking feature (644) may be utilized as would be apparent to one having ordinary skill in the art in view of the teachings herein.

If an operator wishes to remove waveguide (692) for cleaning or other purposes, the operator may actuate locking feature (644) in the upward direction so that locking feature (644) is no longer fixed to cam pin (694). The operator may then pull waveguide (692) in the proximal direction to further remove waveguide (692) from inner tube (670) and outer tube (652)

It should be understood that translation slot (656) of outer tube (652) is dimensioned to allow outer tube (652) to longitudinally travel relative to inner tube (670) such that outer tube (652) does not interfere with cam pin (694) when waveguide (692) is assembled in place and secured by locking feature (644). Therefore, the operator may still open and close a clamp arm relative to a blade. It should also be understood that while one cam pin (694) and one pair of cam slots (672, 654) are utilized in the current example, any suitable number of cam pins (694) and cam slots (672, 654) may be utilized.

C. Waveguide with Clocking Pin

Figure 19:
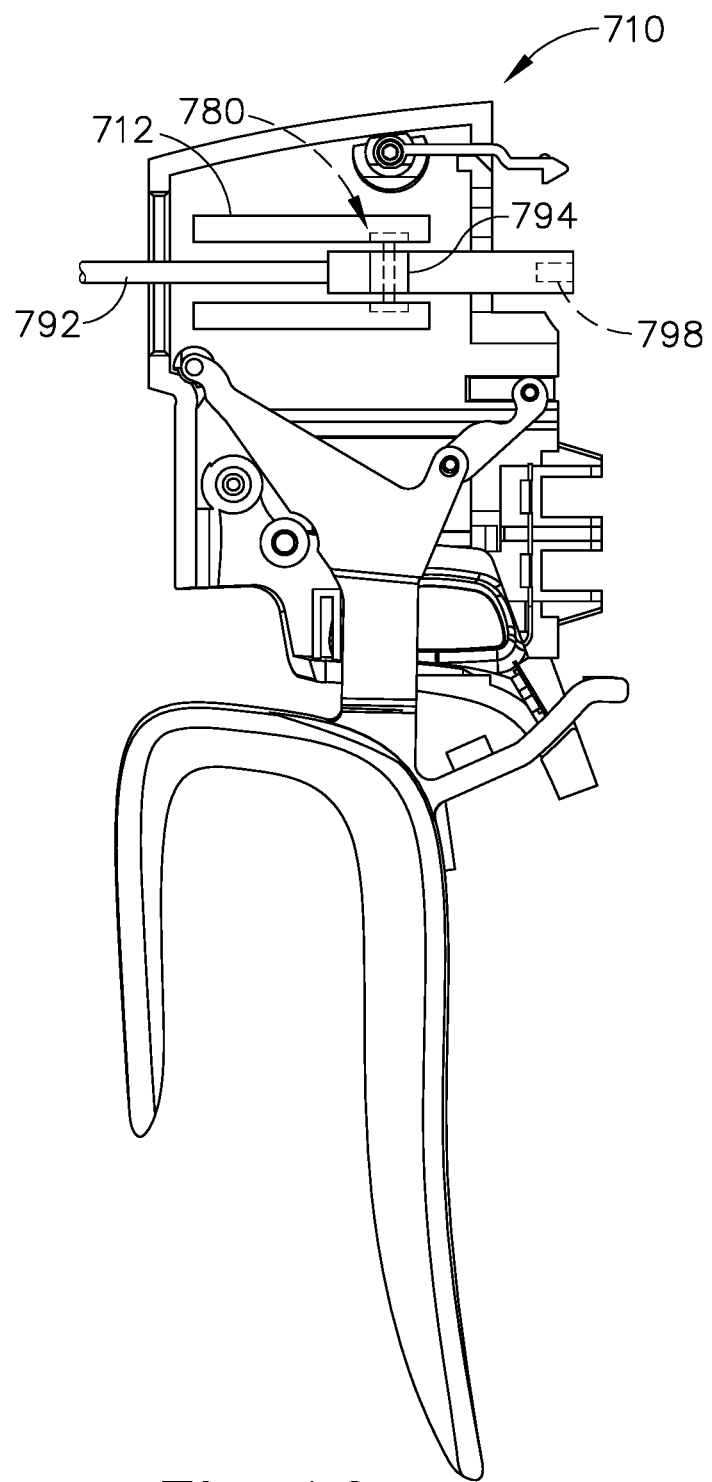
FIG. 19 depicts a side cross-sectional view of an alternative waveguide with a clocking pin and an alternative disposable body that may be readily incorporated into the instrument of FIG. 1.
Figure 22:
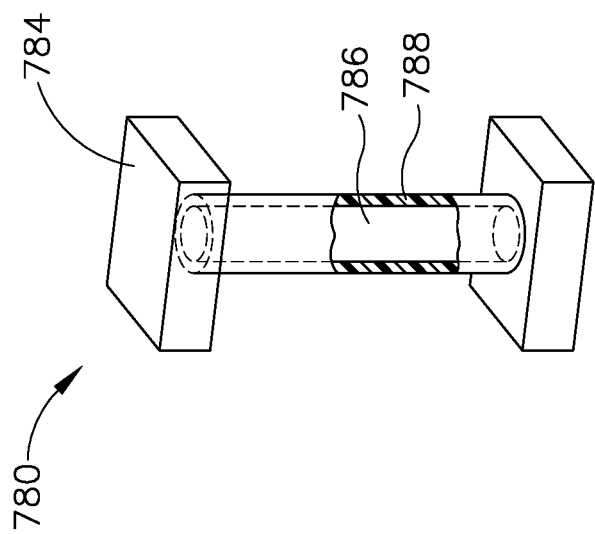
FIG. 22 depicts a perspective view of the clocking pin of FIG. 19.
Figure 20:
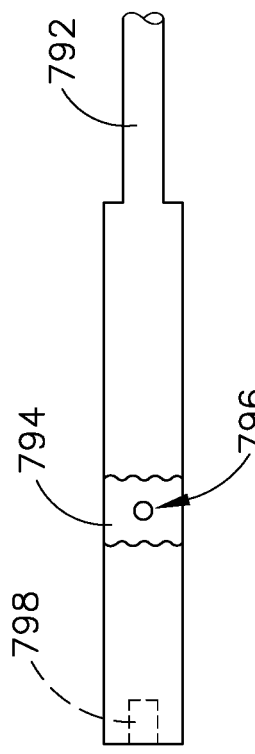
FIG. 20 depicts a top plan view of the waveguide of FIG. 19.
Figure 21:
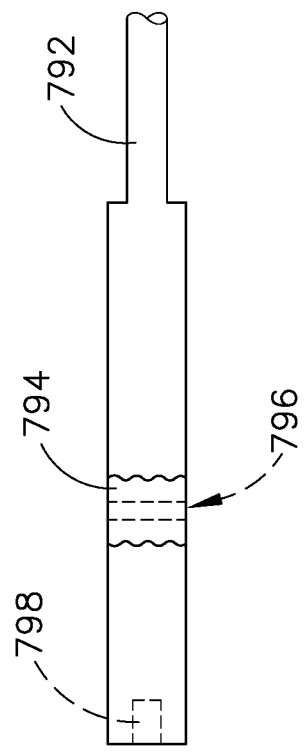
FIG. 21 depicts a side elevational view of the waveguide of FIG. 19.
Figure 26A:
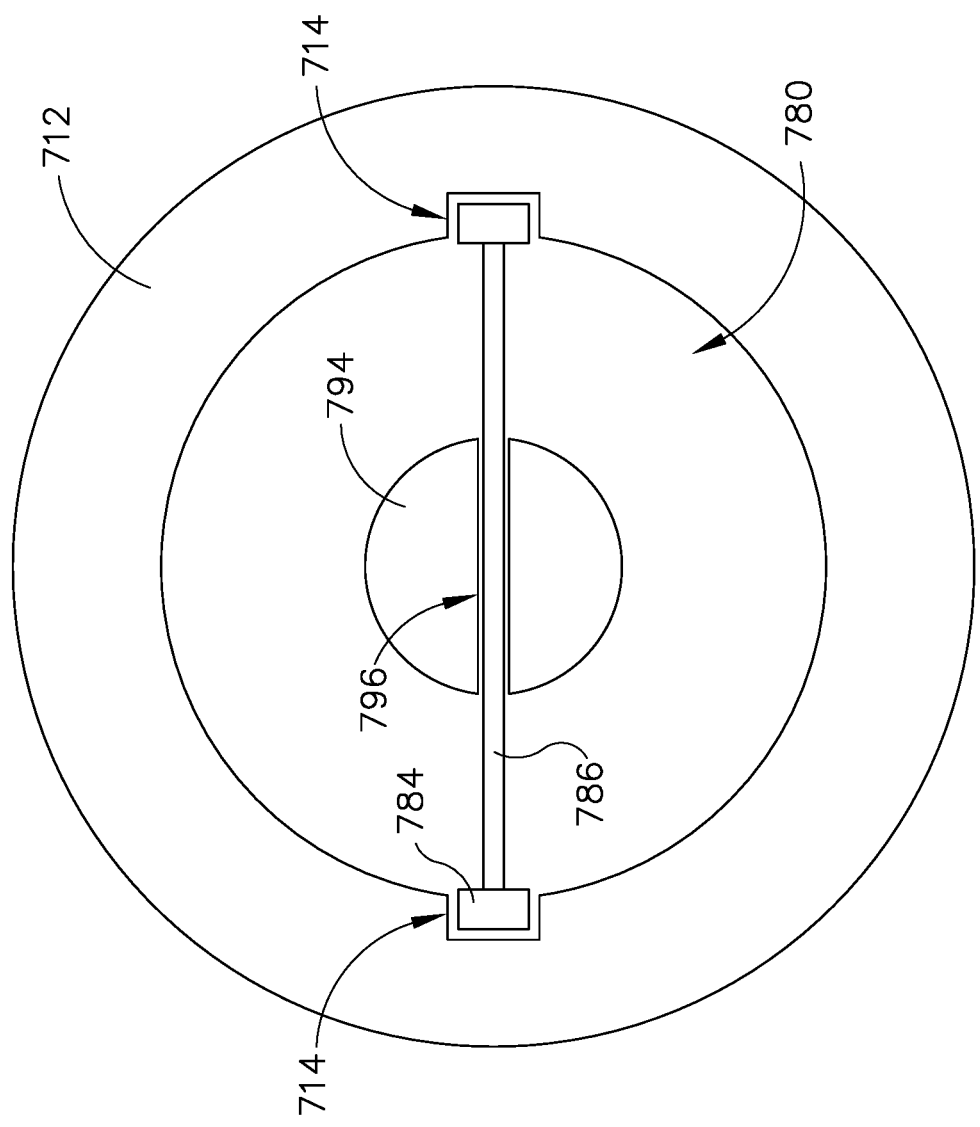
FIG. 26A depicts a cross-sectional view, taken along line 26A-26A of FIG. 25A, of the waveguide and clocking pin of FIG. 19 being initially inserted into the threaded shroud of disposable assembly of FIG. 19.
Figure 26C:
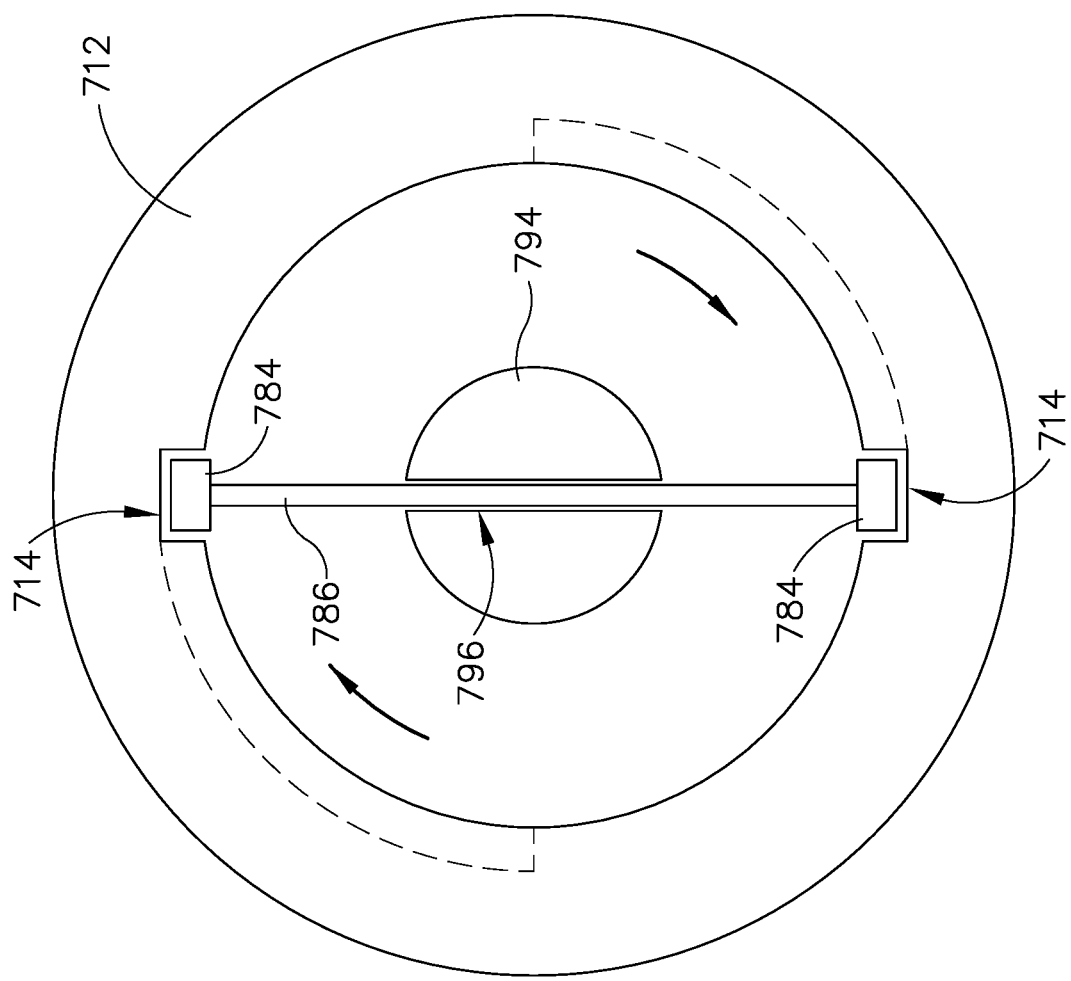
FIG. 26C depicts a cross-sectional view, taken along line 26C-26C of FIG. 25C, of the waveguide and clocking pin of FIG. 19 being locked into the threaded shroud of the disposable assembly of FIG. 19.

FIG. 19 shows an ultrasonic blade (792) and body portion (710) that may be readily incorporated into instrument (10) described above. As best seen in FIGS. 26A-26C, body portion (710) includes a shroud (712) defining a pair of rotating recesses (714). As will be described in greater detail below, rotating recesses (714) of shroud (712) are configured to rotationally and longitudinally align ultrasonic blade (792) relative to the rest of body portion (710).

As best seen in FIGS. 20-24, waveguide (792) includes a threaded recess (798) that is configured to couple waveguide (792) with an ultrasonic transducer (not shown), a silicone portion (794) defining a pin hole (796), and a clocking pin (780) that is configured to fit within pin hole (796) of silicone portion (794). Clocking pin (780) includes a pin (786) surrounded by a silicone overmold (788). Clocking pin (780) further includes a pair of clocking blocks (784) located at the ends of pin (786). Clocking blocks (784) may be made out of a plastic material or contain a plastic overmold. Silicone portion (794) and silicone overmold (788) help isolate ultrasonic waveguide (792) from clocking pin (780). This may help prevent clocking pin (780) from transmitting acoustic vibrations that are transmitted through waveguide (792) to an ultrasonic blade. Clocking pin (780) fits within pin hole (796) in such a way that clocking pin (780) is fixed relative to ultrasonic waveguide (792).

Figure 25A:
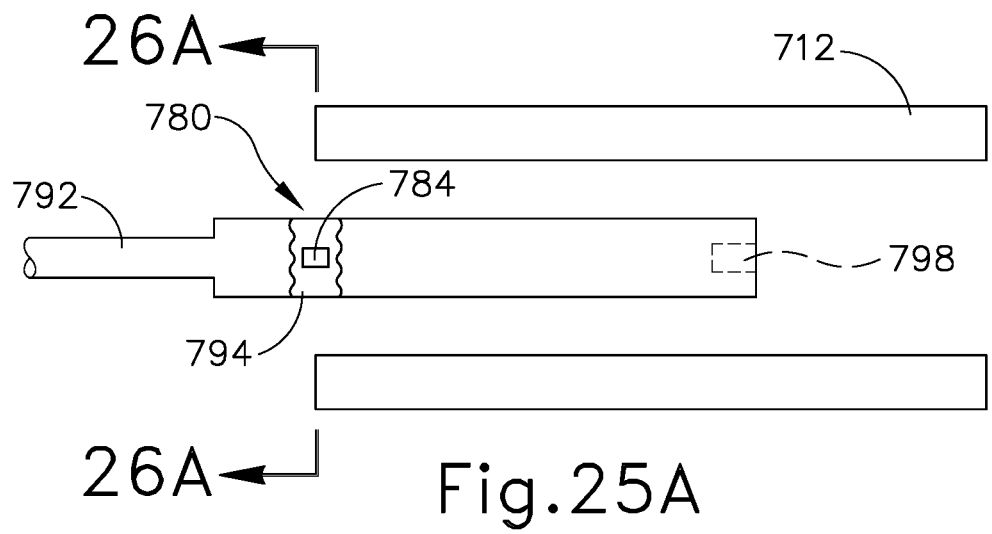
FIG. 25A depicts a cross-sectional side view of the waveguide and clocking pin of FIG. 19 being initially inserted into a threaded shroud of the disposable assembly of FIG. 19.
Figure 25B:
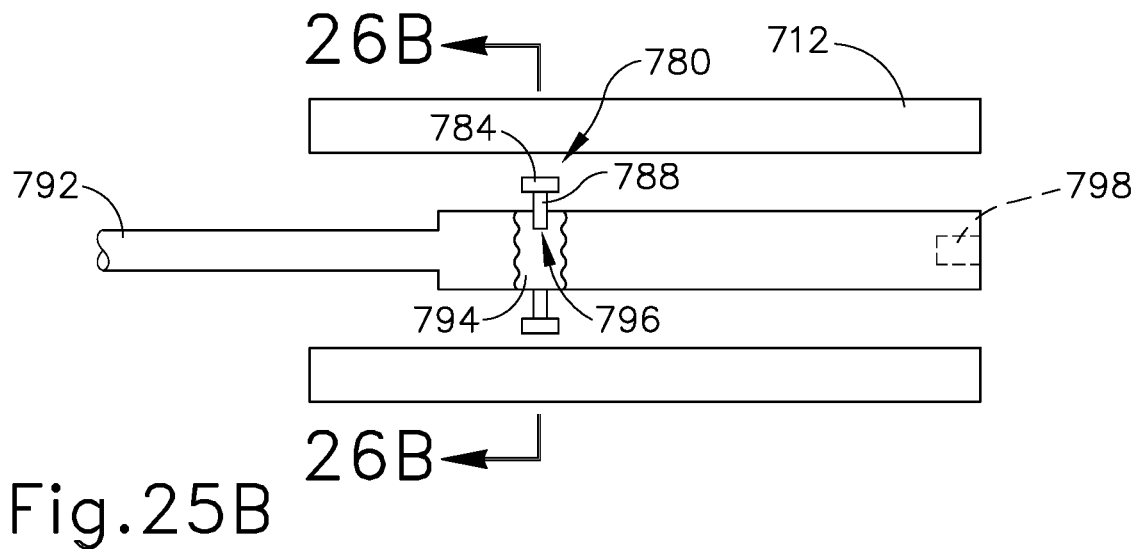
FIG. 25B depicts a cross-sectional side view of the waveguide and clocking pin of FIG. 19 being further rotated into the threaded shroud of the disposable assembly of FIG. 19.
Figure 25C:
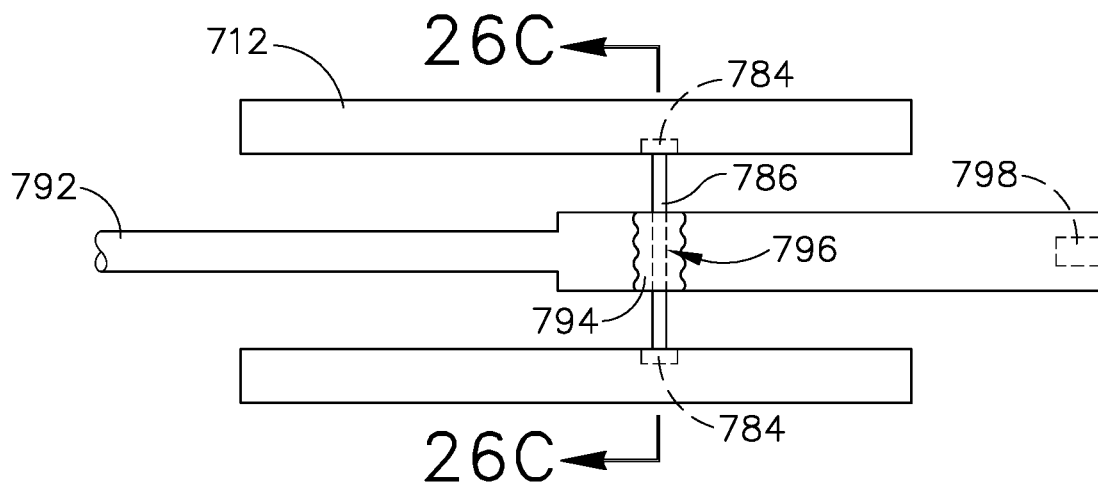
FIG. 25C depicts a cross-sectional side view of the waveguide and clocking pin of FIG. 19 being locked into the threaded shroud of the disposable assembly of FIG. 19.

FIGS. 25A-26C show an exemplary assembly of waveguide (792). First, as shown in FIG. 25A and FIG. 26A, the proximal end of ultrasonic waveguide (792) is inserted into the distal end of shroud (712). Clocking blocks (784) of clocking pin (780) are thereby inserted into the origin of rotating recesses (714). Rotating recesses (714) define respective helical paths within shroud (712). Therefore, as shown in FIG. 25B and FIG. 26B, as waveguide (792) is rotated, clocking blocks (784), and therefore waveguide (792), travel proximally within shroud (712) while rotating to a predetermined angular orientation. Eventually, as shown in FIG. 25C and FIG. 26C, clocking blocks (784) reach the termination of rotating recesses (714). At this point, waveguide (792) cannot further rotate or travel proximally relative to shroud (712). Because shroud (712) is fixed relative to the rest of body (710), waveguide (792) will be uniformly placed in the same longitudinal and angular position every time waveguide (792) is "clocked" within shroud (712). An operator may remove waveguide (792) for cleaning and reinsert waveguide (792) back into shroud (712) at the exact location for subsequent use.

While the present example has waveguide (792) being inserted at the distal end of shroud (712), alternatively waveguide (792) may also be configured to be inserted in the proximal end of shroud (712).

D. Tethered Waveguide

Figure 27A:
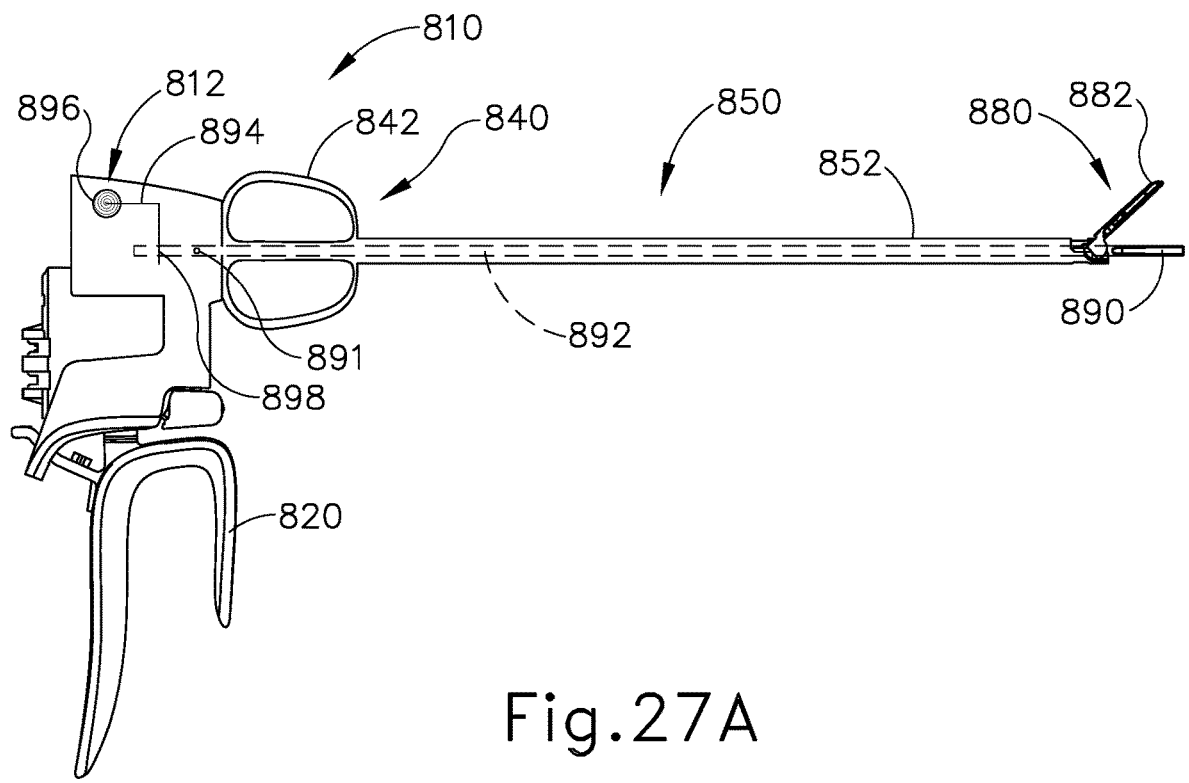
FIG. 27A depicts a side cross-sectional view of another alternative shaft assembly and disposable assembly that may be readily incorporated into the instrument of FIG. 1.
Figure 27B:
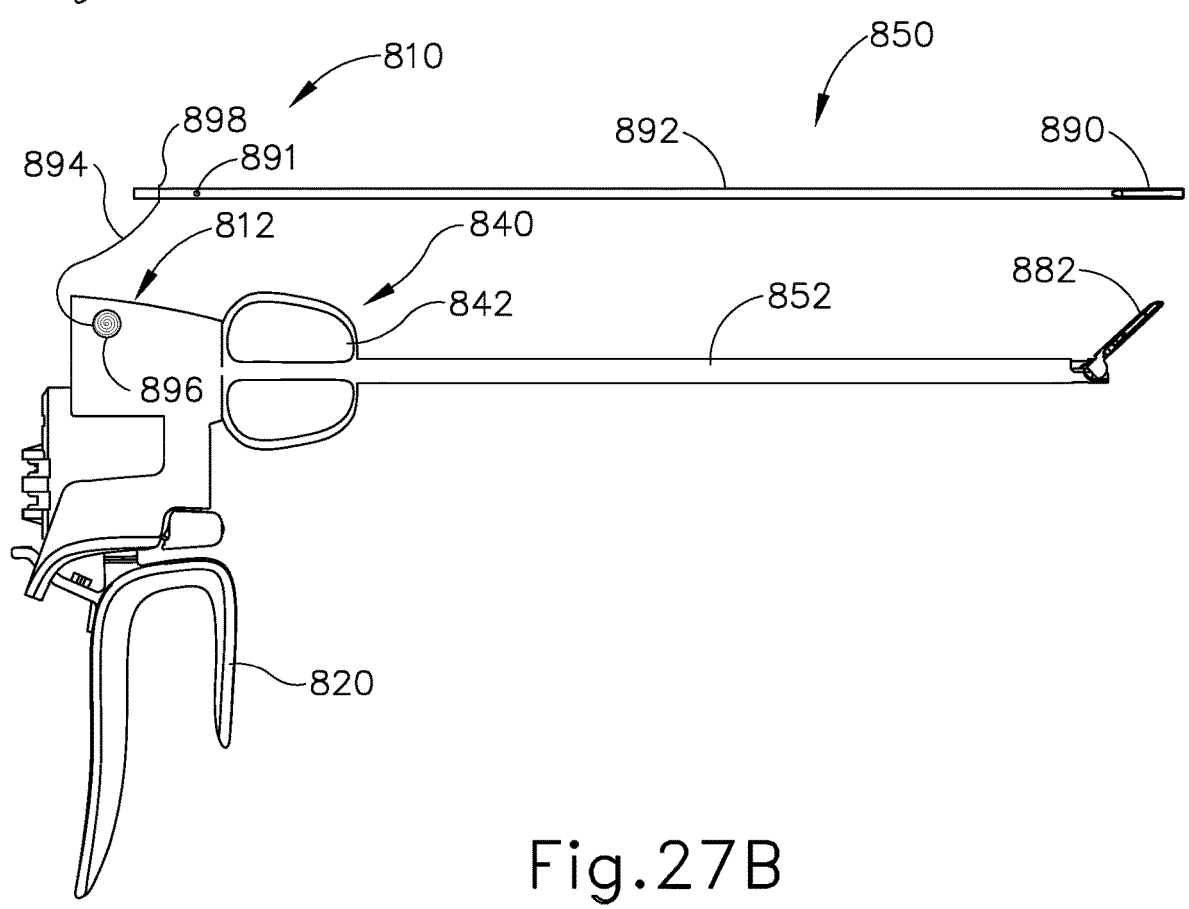
FIG. 27B depicts a side cross-sectional view of the shaft assembly of disposable assembly of FIG. 27A, where the acoustic waveguide is removed from the rest of the shaft assembly but remains tethered.

FIGS. 27A-27B show an alternative body (810), shaft assembly (850), and end effector (880) that may be readily incorporated into instrument (10) described above. Shaft assembly (850) and end effector (880) are substantially similar to shaft assembly (150) and end effector (180) described above, with differences described below. Shaft assembly (850) includes an outer tube (852), an inner tube (not shown), a waveguide (892) and a rotation assembly (840); which are substantially similar to outer tube (152), inner tube (170), waveguide (192) and rotation assembly (540) described above. Rotation assembly (840) includes a rotation knob (842) substantially similar to rotation knob (542) described above. Waveguide (892) defines a pin hole (891) that is configured to be used in coupling waveguide (892) to body (810). End effector (880) includes a clamp arm (882) and an acoustic blade (890) substantially similar to clamp arm (182) and acoustic blade (190) mentioned above.

Body (810) includes a trigger (820), a tether (894) connected to waveguide (892) at a connection point (898), and a tether housing (812) that stores a coiled portion (896) of tether (894). Tether (894) extends from coiled portion (896) in such a way that portions of tether (894) may extend out of coiled portion (896), as shown in FIG. 27B. Coiled portion (896) may have recoil function, such that tugging on the portion of tether (894) extending from coiled portion (896) encourages coiled portion (896) to recoil excess lengths of tether (894). As shown in FIG. 27B, connection point (898) couples tether (894) with waveguide (892) such that waveguide (892) can be removed relative to the rest of shaft assembly (850), but cannot be removed entirely relative to body (810). In other words, even if waveguide (892) is removed from shaft assembly (850) for cleaning, waveguide (892) cannot be completely detached from body (810) due to tether (894). Connection point (898) may consist of a groove on waveguide (892) in which tether (894) is tied around. Alternatively, connection point (898) may comprise an overmold of silicone on the portion of tether (894) in contact with waveguide (892). Various other suitable ways in which tether (894) may be secured to waveguide (892) will be apparent to one having ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a shaft assembly defining a longitudinal axis, wherein the shaft assembly comprises: (i) a first coupling member, and (ii) a second coupling member, wherein the first coupling member and the second coupling member are configured to flex toward each other from a first position to a second position, wherein the first coupling member and the second coupling member define a pivot axis in the first position; and (b) an end effector comprising: (i) an ultrasonic blade extending from the shaft assembly, (ii) a lamp arm configured to couple or decouple with the shaft assembly when the first coupling member and the second coupling member are in the second position, wherein the clamp arm is configured to pivot toward and away the ultrasonic blade about the pivot axis when the first coupling member and the second coupling member are in the first position.

EXAMPLE 2

The apparatus of Example 1, wherein the clamp arm comprises a first integral pin and a second integral pin, wherein the first integral pin is configured to couple or decouple with the first coupling member when the first coupling member and the second coupling member are in the second position, wherein the second integral pin is configured to couple or decouple with the second coupling member when the first coupling member and the second coupling member are in the second position.

EXAMPLE 3

The apparatus of Example 2, wherein the first integral pin and the second integral pin define a lateral gap, wherein the width of the ultrasonic blade is smaller than the lateral gap.

EXAMPLE 4

The apparatus of any one or more of Examples 1 through 3, wherein the first coupling member and the second coupling member define a longitudinal channel, wherein the longitudinal channel is wider in the first position than the second position.

EXAMPLE 5

The apparatus of Example 4, wherein the first coupling member comprises a tab, wherein the tab extends over the longitudinal channel toward the second coupling member.

EXAMPLE 6

The apparatus of Example 5, wherein the tab is configured to be fixed to the second coupling member, wherein the tab is configured to prevent the first coupling member and the second coupling member from flexing to the second position when the tab is fixed to the second coupling member.

EXAMPLE 7

The apparatus of any one or more of Examples 4 through 6, wherein the shaft assembly further comprises a cap.

EXAMPLE 8

The apparatus of Example 7, wherein the cap comprises a spacer, wherein the spacer is dimensioned to fit within the longitudinal channel when the first coupling member and the second coupling member are in the first position.

EXAMPLE 9

The apparatus of Example 8, wherein the spacer is configured to prevent the first coupling member and the second coupling member from flexing from the first position to the second position when the spacer is within the longitudinal channel.

EXAMPLE 10

The apparatus of Example 9, wherein the cap comprises a first flange and a second flange, wherein the first flange is configured to rest on top of the first coupling member, wherein the second flange is configured to rest on top of the second coupling member.

EXAMPLE 11

The apparatus of Example 10, wherein the first flange is configured to fix to the first coupling member, wherein the second flange is configured to fix to the second coupling member.

EXAMPLE 12

The apparatus of any one or more of Examples 9 through 11, wherein the spacer defines a first longitudinal slot and a second longitudinal slot, wherein the first longitudinal slot is configured to house a portion of the first coupling member, wherein the second longitudinal slot is configured to house a portion of the second coupling member.

EXAMPLE 13

The apparatus of any one or more of Examples 9 through 12, wherein the cap further comprises a tab, wherein the first coupling member and the second coupling member further define a locking channel, wherein the tab is dimensioned to fit within the locking channel, wherein the tab is configured to prevent longitudinal movement of the cap when the tab is within the locking channel.

EXAMPLE 14

The apparatus of Example 13, wherein the cap further comprises a resilient member positioned between the tab and the spacer.

EXAMPLE 15

An apparatus comprising: (a) an end effector comprising an ultrasonic blade; and (b) a shaft assembly defining a longitudinal axis, wherein the ultrasonic blade extends from the shaft assembly, wherein the shaft assembly comprises: (i) a first tube, (ii) an acoustic waveguide extending through the first tube, wherein the acoustic waveguide is unitarily attached to the ultrasonic blade, wherein the acoustic waveguide is configured to be removed from the first tube, and (iii) a locating feature, wherein the locating feature is configured to orient the acoustic waveguide relative to the first tube along the longitudinal axis and about the longitudinal axis.

EXAMPLE 16

The apparatus of Example 15, wherein the locating feature comprises a key lock, wherein the acoustic waveguide defines a recess configured to mate with the key lock to orient the acoustic waveguide relative to the first tube.

EXAMPLE 17

The apparatus of Example 16, wherein the key lock is biased to engage the recess defined by the acoustic waveguide.

EXAMPLE 18

The apparatus of any one or more of Examples 15 through 17, wherein the locating feature comprises a cam slot defined by the first tube, wherein the acoustic waveguide comprises a cam pin configured to be inserted into the cam slot.

EXAMPLE 19

The apparatus of Example 18, wherein the shaft assembly further comprises a locking feature configured to selectively fix to the cam pin.

EXAMPLE 20

An apparatus comprising: (a) a body portion; (b) a shaft assembly extending distally from the body portion, wherein the shaft assembly comprises: (i) an acoustic waveguide, and (ii) a tube, wherein the acoustic waveguide is configured to fit coaxially within the tube, wherein the acoustic waveguide is configured to be removed from the tube; and (c) a tether, wherein a first end of the tether is coupled with the body portion, wherein a second portion of the tether is coupled with the acoustic waveguide, wherein the tether has a length configured to enable removal of the acoustic waveguide from the tube while still coupling the acoustic waveguide with the body portion.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector including an ultrasonic blade; and
   (b) a shaft assembly defining a longitudinal axis and having the ultrasonic blade distally projecting therefrom, wherein the shaft assembly includes:
      a first tube,
      (ii) an acoustic waveguide extending through the first tube, wherein the acoustic waveguide is unitarily attached to the ultrasonic blade and configured to be removed from the first tube, and
      (iii) a lock configured to releasably secure the acoustic waveguide relative to the first tube longitudinally along the longitudinal axis and angularly about the longitudinal axis,
      wherein the lock includes a key lock configured to selectively move from a locked position toward an unlocked position, wherein the key lock in the locked position is configured to releasably secure the first tube relative to the acoustic waveguide, and wherein the key lock in the unlocked position is configured to release the first tube relative to the acoustic waveguide such that the acoustic waveguide is configured to be longitudinally removed from the first tube,
      wherein the key lock is resiliently biased toward at least one of the locked or unlocked positions.

2. The surgical instrument of claim 1, wherein the key lock in the locked position is engaged with the acoustic waveguide to longitudinally and angularly secure the first tube relative to the acoustic waveguide, and wherein the key lock in the unlocked position is disengaged from the acoustic waveguide such that the acoustic waveguide is configured to be longitudinally removed from the first tube.

3. The surgical instrument of claim 2, wherein the acoustic waveguide includes a first keyed flat, and wherein the key lock is configured to engage the first keyed flat in the locked position.

4. The surgical instrument of claim 3, wherein the key lock includes a handle and a first lock fork, wherein the first lock fork extends from the handle and is configured to engage the first keyed flat with the key lock in the locked position.

5. The surgical instrument of claim 4, wherein the acoustic waveguide includes a second keyed flat, and wherein the key lock includes a second lock fork, and wherein the second lock fork extends from the handle and is configured to engage the second keyed flat with the key lock in the locked position.

6. The surgical instrument of claim 5, wherein the first and second keyed flats are angularly opposed to each other about the longitudinal axis on the acoustic waveguide.

7. The surgical instrument of claim 6, wherein the first lock fork has a first fork portion, wherein the second lock fork has a second fork portion, and wherein the first fork portion is parallel with the second fork portion.

8. The surgical instrument of claim 3, wherein the acoustic waveguide defines an outer profile surrounding the longitudinal axis, and wherein at least a portion of the first keyed flat is radially inward of the outer profile.

9. The surgical instrument of claim 2, wherein the first tube at least partially defines a key slot, wherein the key slot receives at least a portion of the key lock as the key lock moves between the locked and unlocked positions.

10. The surgical instrument of claim 9, wherein the shaft assembly further includes a second tube that receives the first tube, and wherein the second tube further defines the key slot.

11. The surgical instrument of claim 9, wherein the shaft assembly further includes a rotation knob and a sleeve, wherein the rotation knob is configured to rotate about the longitudinal axis and is rotatably secured relative to the first tube, wherein the sleeve extends from the rotation knob along the longitudinal axis, and wherein the sleeve further defines the key slot.

12. The surgical instrument of claim 11, wherein the at least the portion of the key lock is in the key slot of the sleeve in the unlocked and locked positions.

13. The surgical instrument of claim 11, further comprising a body, wherein the rotation knob is rotatably mounted to the body.

14. The surgical instrument of claim 1, wherein the key lock is resiliently biased toward the locked position.

15. A surgical instrument, comprising:
   (a) an end effector including an ultrasonic blade; and
   (b) a shaft assembly defining a longitudinal axis and having the ultrasonic blade distally projecting therefrom, wherein the shaft assembly includes:
      (i) a first tube at least partially defining a key slot,
      (ii) an acoustic waveguide extending through the first tube, wherein the acoustic waveguide is unitarily attached to the ultrasonic blade and configured to be removed from the first tube, wherein the acoustic waveguide includes a first keyed flat and a second keyed flat, and
      (iii) a key lock having a handle with a first lock fork and a second lock fork, wherein the key lock is configured to selectively move from a locked position toward an unlocked position, wherein the first and second lock forks are respectively engaged with the first and second keyed flats in the locked position to longitudinally and angularly secure the first tube relative to the acoustic waveguide, and wherein the first and second lock forks are respectively disengaged from the first and second keyed flats in the unlocked position such that the acoustic waveguide is configured to be longitudinally removed from the first tube
      wherein the key slot receives at least a portion of the key lock as the key lock moves between the locked and unlocked positions.

16. The surgical instrument of claim 15, wherein the shaft assembly further includes a rotation knob and a sleeve, wherein the rotation knob is configured to rotate about the longitudinal axis and is rotatably secured relative to the first tube, wherein the sleeve extends from the rotation knob along the longitudinal axis, and wherein the sleeve further defines the key slot.

17. The surgical instrument of claim 1, wherein the key lock is resiliently biased toward at least one of the locked or unlocked positions.

18. A surgical instrument, comprising:
(a) an end effector including an ultrasonic blade; and
(b) a shaft assembly defining a longitudinal axis and having the ultrasonic blade distally projecting therefrom, wherein the shaft assembly includes:
   (i) a first tube at least partially defining a key slot,
   (ii) a tubular portion that receives the first tube and further defining the key slot,
   (iii) an acoustic waveguide extending through the first tube, wherein the acoustic waveguide is unitarily attached to the ultrasonic blade and configured to be removed from the first tube, and
   (iv) a lock configured to releasably secure the acoustic waveguide relative to the first tube longitudinally along the longitudinal axis and angularly about the longitudinal axis,
wherein the lock includes a key lock configured to selectively move from a locked position toward an unlocked position, wherein the key lock in the locked position is configured to releasably secure the first tube relative to the acoustic waveguide, and wherein the key lock in the unlocked position is configured to release the first tube relative to the acoustic waveguide such that the acoustic waveguide is configured to be longitudinally removed from the first tube, and
wherein the key slot receives at least a portion of the key lock as the key lock moves between the locked and unlocked positions.

19. The surgical instrument of claim 18, wherein the tubular portion includes a second tube that receives the first tube, and wherein the second tube further defines the key slot.

20. The surgical instrument of claim 18, wherein the tubular portion includes a rotation knob and a sleeve, wherein the rotation knob is configured to rotate about the longitudinal axis and is rotatably secured relative to the first tube, wherein the sleeve extends from the rotation knob along the longitudinal axis, and wherein the sleeve further defines the key slot.

* * * * *